United States Patent [19]

Gollamudi et al.

[11] Patent Number: 5,219,867
[45] Date of Patent: Jun. 15, 1993

[54] PLATELET AGGREGATION INHIBITORY AGENTS

[75] Inventors: Ramachander Gollamudi; Zixia Feng, both of Memphis, Tenn.

[73] Assignee: Research Corporation Technologies, Inc., Tucson, Ariz.

[21] Appl. No.: 927,684

[22] Filed: Aug. 10, 1992

Related U.S. Application Data

[63] Continuation-in-part of Ser. No. 808,000, Dec. 16, 1991, abandoned.

[51] Int. Cl.[5] ............... C07D 211/32; A61K 31/445
[52] U.S. Cl. ...................................... 514/316; 546/189
[58] Field of Search ........................ 546/189; 514/316

[56] References Cited

U.S. PATENT DOCUMENTS 4,634,709  1/1987  Lasslo et al. .................. 514/316
4,657,917  4/1987  Lasslo et al. .................. 514/316

OTHER PUBLICATIONS

Gollamudi, et al., Chirality, 1991, 3, 480-483.

Primary Examiner—Marianne M. Cintins
Assistant Examiner—Michael B. Hydorn
Attorney, Agent, or Firm—Scully, Scott, Murphy & Presser

[57] ABSTRACT

The present invention relates to substantially pure stereoisomers of a compound of the formula:

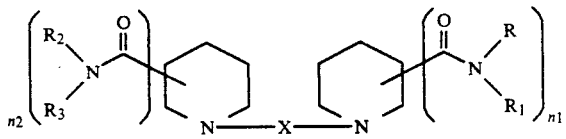

wherein $n_1$ and $n_2$ are the same or different and are 1 or 2; X is alkyl ($C_1$-$C_{10}$), aryl ($C_6$-$C_{10}$) or aralkyl ($C_7$-$C_{12}$); and wherein R, $R_1$, $R_2$ and $R_3$ are the same or different and are chosen from H, alkyl ($C_1$-$C_{10}$), aryl ($C_6$-$C_{10}$), aralkyl ($C_7$-$C_{12}$), or a heterocyclic group, and addition salts thereof with pharmaceutically acceptable acids. The invention also relates to a method for the inhibition of blood platelet aggregation in a blood supply comprising administering to said blood supply a blood platelet aggregation inhibiting amount of the compounds of the present invention.

84 Claims, 16 Drawing Sheets

PLATELET AGGREGATION INHIBITORY AGENTS

The invention was made with Government support under Grant No. HL-22236 awarded by the National Institutes of Health. The Government has certain rights in the invention.

CROSS REFERENCE TO A RELATED APPLICATION

This is a continuation-in-part of copending U.S. patent application Ser. No. 808,000, filed on Dec. 16, 1991, now abandoned.

BACKGROUND OF THE INVENTION

The present invention generally relates to certain compounds useful as platelet aggregation inhibitory agents.

Antithrombotic agents are substances that prevent the formation of a thrombus. There are two different types of thrombi; venous thrombus and arterial thrombus. The first is the red thrombus which consists of a fibrin network entrapping the formed elements of the blood. The second one is the white thrombus which is composed mainly of platelets. All forms of venous thrombus and embolism result from red thrombus. Thrombotic and thromboembolic events, which manifest as myocardial infarction and stroke, remain the leading cause of death and disability in the United States.

Thromboembolic disorders have been shown to be directly related to the susceptibility of blood platelets to adenosine diphosphate and thrombin induced platelet aggregation and to other adhesion-release-aggregation chain reactions. Certain animal species wearing prosthetic devices or whose blood is exposed to biomaterials during renal dialysis, blood oxygenation, cardiac catheterization, etc. are especially predisposed to thromboembolic disorders.

Certain chemical compounds are known to inhibit platelet aggregation and are classified as antithrombotic agents. Many of these compounds are not employed, however, because of their alternative therapeutic effects. Drugs that have shown activity in inhibiting platelet aggregation belong to the following chemical groups:

1. Arylakanoic acids & derivatives: e.g. ibuprofen;
2. Clofibric acid derivatives: e.g. clofibrate;
3. Dextrans: e.g. dextran 40;
4. Imidazole derivatives & isosteres: e.g. dazmegrel;
5. Prostaglandins: e.g. azaprostanoic acid;
6. Phthalazinecarboxylic acid derivatives: e.g. anagrelide;
7. Pyrazole derivatives: e.g. sulfinpyrazone, nafazatrom;
8. Pyrimidine derivatives: e.g. dipyridamole;
9. Salicylates: e.g. aspirin;
10. Miscellaneous structures: e.g. amipizone, cilostazol, ticlopidine, bencyclane, picotamide, etc.

Inhibitors of platelet aggregation generally act by one of the following mechanisms: (1) inhibition of arachidonic acid-dependent aggregation: (a) cyclooxygenase inhibitors: arylalkanoic acids and derivatives, pyrazole derivatives, and salicylates; (b) thromboxane synthetase inhibitors: imidazole derivatives and isosteres, and phthalazinecarboxylic acid derivatives; (c) thromboxane $A_2$ antagonists; (d) prostacyclin activator: nafazatrom; or (2) inhibition of arachidonic acid-independent aggregation: (a) cyclic AMP phosphodiesterase inhibitors; cilostazol, and pyrimidine derivatives; (b) adenylate cyclase activators; prostaglandins and ticlopidine.

Accordingly, it is known that a large series of aryl and alkyl bis-piperidine compounds exhibit platelet aggregation inhibitory activity, as described by U.S. Pat. Nos. 4,634,709 and 4,657,917. While the exact mechanism of action is not clearly understood, the amphiphilic structure of these compounds suggests that they may insert themselves into the plasma membrane and other membrane bilayers and interrupt normal transmembrane ion-mediated signals which would normally lead to platelet aggregation. These events, being devoid of ligand-receptor interactions or enzyme inhibition, are not generally thought of as being dependent on the chiral influences of the active agents. The present inventors have, however, unexpectedly discovered that the optical isomers of such compounds are not equipotent.

It is therefore an object of the present invention to provide a composition and method for inhibiting blood platelet aggregation thereby being useful for the treatment of thromboembolic disorders.

It is a further object of the invention to provide a stereoisomer of anti-thromboembolic compound with an improved ratio of therapeutic potency to toxicity.

SUMMARY OF THE INVENTION

The present invention is directed to stereoisomers exhibiting blood platelet aggregation inhibitory activity. These stereoisomers contain two dialkyl carbamoyl piperidino groups connected by a bridging unit. Chiral centers are located on the carbon atoms of the piperidino group bonded to the carbamoyl groups. Thus, a minimum of four stereoisomers are present, i.e., (R,R), (S,S), (R,S) and (S,R). The stereoisomers of the present invention exhibit, in the light absorbing region, a positive or a negative cotton effect in circular dichroic spectra (CD).

A preferred embodiment is directed to stereoisomers described hereinabove, containing a plane of symmetry. In this embodiment, the plane of symmetry passes through the bridging unit connecting the two dialkylcarbamoyl piperidino groups.

The invention also relates to methods for the inhibition of blood platelet aggregation in a blood supply comprising administering to said blood supply a blood platelet aggregation inhibiting amount of the stereoisomers described hereinabove.

The invention also relates to methods for the inhibition of blood platelet aggregation in an animal in need thereof comprising the administration to said animal a blood platelet aggregation inhibitory amount of the stereoisomers described hereinabove.

The invention also relates to a pharmaceutical composition in unit dosage form suitable for usage in the above described method comprising a pharmaceutically acceptable carrier and a blood platelet aggregation inhibitory amount of the stereoisomers described hereinabove.

DETAILED DESCRIPTION OF THE INVENTION

Figure 1:
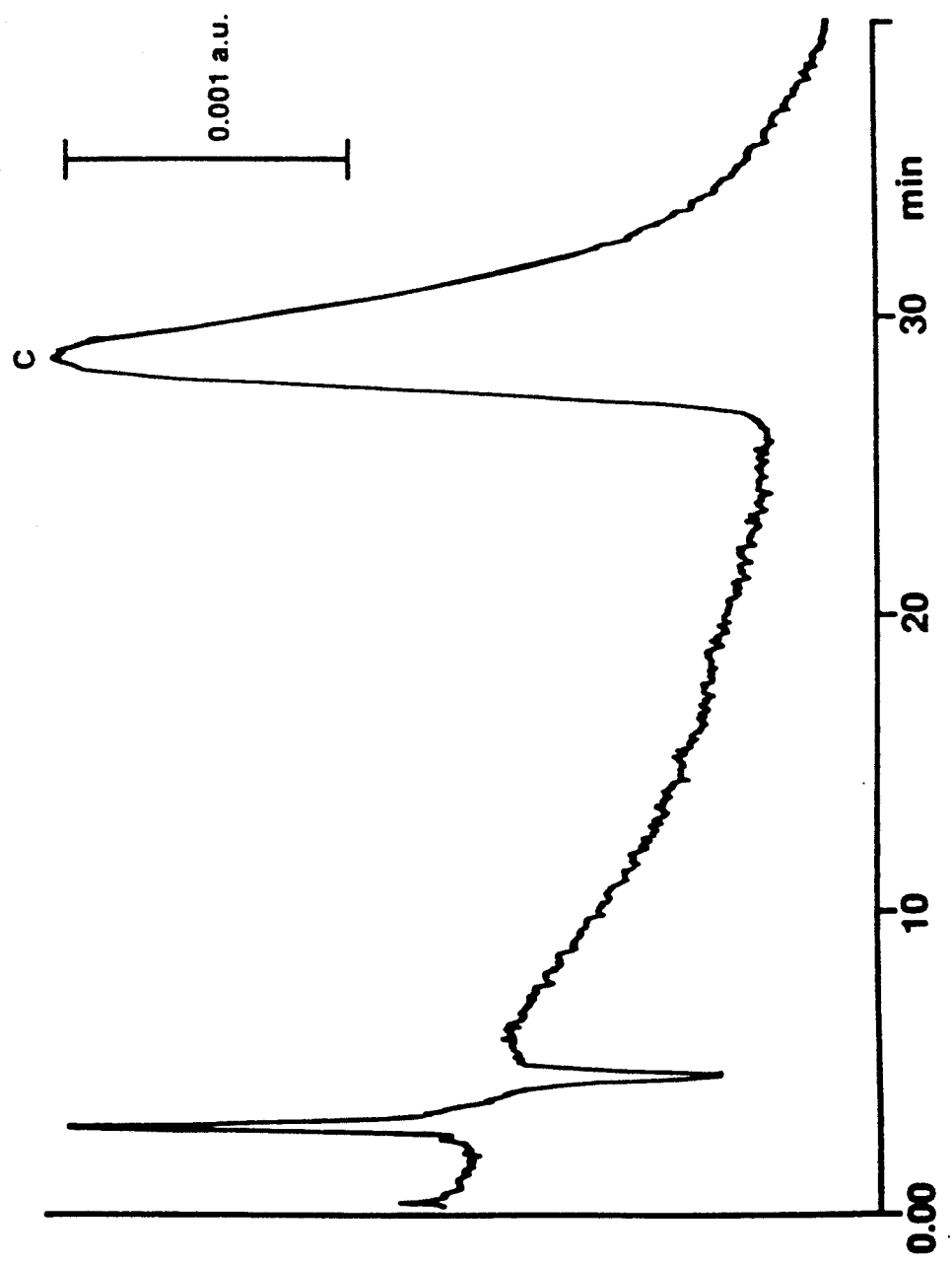
FIG. 1 is a chromatogram showing the purity of IC (0.5 mg injected) obtained by the fractional crystallization of I free base 1. HPLC Conditions: Chiral-AGP semipreparative column, 150×10 mm (5 μm) with a diol precolumn 10 mm×10 mm (5 μm). Mobile phase was 0.025M PB (pH 6.5) containing 0.025M TBA HSO₄, at a flow rate of 3.6 ml/min.

The antithromboembolic compounds within the scope of the present invention are substantially pure stereoisomers of compounds represented by formula:

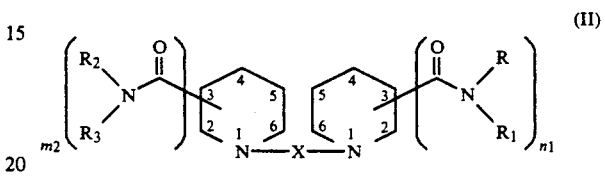

(II)

where X is alkyl ($C_1$-$C_{10}$), aryl ($C_6$ to $C_{10}$), or aralkyl ($C_7$-$C_{12}$); and wherein R, $R_1$, $R_2$ and $R_3$ are the same or different and are chosen from H, alkyl ($C_1$-$C_{10}$), aryl ($C_6$-$C_{10}$), aralkyl ($C_7$-$C_{12}$), or a heterocyclic group, and addition salts thereof with pharmaceutically acceptable acids. Alternatively, said R and $R_1$ groups in conjunction with the nitrogen to which they are attached, can form a 5 or 6 membered heterocyclic ring, which may be optionally substituted with alkyl, aryl and/or aralkyl groups. Similarly, $R_2$ and $R_3$, in conjunction with the nitrogen to which they are attached, can form a 5 or 6 membered heterocyclic ring which may be optionally substituted with alkyl, aryl or aralkyl groups. These heterocyclic rings contemplated herein are nitrogen containing heterocyclics as defined hereinbelow and they may be saturated, unsaturated or heteroaromatic. The preferred groups include piperidino and 1,4 morpholine. $n_1$ and $n_2$ may be the same or different and are equal to 1 or 2. When Compound II is di-substituted, i.e., $n_1=n_2=2$, the preferred positions of substitution are at the 3 and 5 positions of the piperidine ring. In one embodiment, the present invention contemplates stereoisomers of compounds of General Formula (II) which exhibit, in the light absorbing region, a positive cotton effect in circular dichroic spectra (CD). In a second embodiment the present invention contemplates stereoisomers of compounds of General Formula (II) which exhibit, in the light absorbing region, a negative cotton effect in circular dichroic spectra. The compounds of formula (II) contain at least two asymmetric centers (the carbon atoms on the piperidino ring attached to the aminocarbonyl substituent) and can exist in a minimum of four stereoisomer forms, (R,R), (R,S), (S,R) and (S,S). All of the stereoisomers are contemplated by the present invention. However, it is preferred that the present compounds be in the (R,R) or (S,S) configuration.

The term "substantially pure stereoisomer" as employed herein is meant to indicate the existence of a particular stereoisomer, in at least 60% purity; preferably 75% purity; and still more preferably at least 95% purity. As defined herein, the terms R or S refer to the configuration at the carbon atoms of the piperidino ring which is attached to the carbamoyl group. Since each piperidino ring in the formulae used herein have at least one such carbon atom, there are at least four possible enantiomers at the positions. Consequently, if a compound is in the S,S configuration, it means that the configuration at each of these carbon atoms is in the S-configuration. Similarly, if a compound is in the R,R configuration, it means that each of these carbon atoms is in the R-configuration.

In another preferred embodiment, the present invention contemplates substantially pure stereoisomers of compounds represented by the general formula:

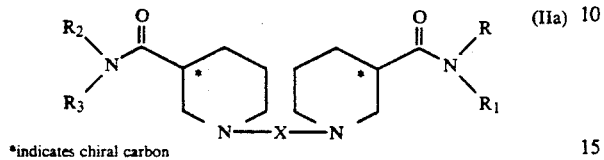

*indicates chiral carbon wherein X is alkyl ($C_1$–$C_{10}$), aryl ($C_6$–$C_{10}$) or aralkyl ($C_7$–$C_{12}$); and, wherein R, $R_1$, $R_2$ and $R_3$ are the same or different and are chosen from H, alkyl ($C_1$–$C_{10}$), aryl ($C_6$–$C_{10}$), aralkyl ($C_7$–$C_{12}$), or a heterocyclic group, and addition salts thereof with pharmaceutically acceptable acids. Alternatively, said R and $R_1$ groups, in conjunction with the nitrogen to which they are attached, can form a 5 or 6 membered heterocyclic ring, which may be optionally substituted with alkyl, aryl and aralkyl groups. Similarly, $R_2$ and $R_3$ in conjunction with the nitrogen to which they are attached can form a 5 or 6 membered heterocyclic ring, which may be optionally substituted with alkyl, aryl and aralkyl groups. These heterocyclic rings may be saturated, unsaturated or heteroaromatic. The preferred groups include piperidino and 1,4 morpholine. In one embodiment, the present invention contemplates stereoisomers of compounds of General Formula (IIa) which exhibit, in the light absorbing region, a positive cotton effect in circular dichroic spectra. In a second embodiment, the present invention contemplates stereoisomers of compounds of General Formula (IIa) which exhibit, in the light absorbing region, a negative cotton effect in circular dichroic spectra. The compounds of Formula II contain two asymmetric centers and can exist in four stereoisomer forms (R,R), (R,S), (S,R) or (S,S). All of the stereoisomers are contemplated by the present invention. However, it is preferred that the compounds of the present invention be the (R,R) or (S,S) enantiomer.

As employed herein, the heterocyclic group contains at least one nitrogen, sulphur or oxygen ring atom, but may also include one or several of said atoms, but preferably one to four hetero ring atoms, and most preferably one to two hetero ring atoms. The heterocyclic group contemplated by the present invention includes heteroaromatics and saturated and partially saturated heterocyclic compounds. The heterocyclics may be monocyclic or bicyclic. They may contain up to 10 ring atoms and up to a total of 9 ring carbon atoms. The heterocyclic groups also include the benzoheterocyclics. Representative heterocyclics include thiazole, oxazole, furan, pyridine, pyridazine, pyrimidine, piperidine, thiophene, pyrrole, isothiazole, pyrazine, piperazine, benzothiophene, benzofuran, purine, indole, benzoxazole, indazole, quinoline, isoquinoline, oxazine, oxathiazine, morpholine and the like.

The alkyl groups when used alone or in combination with other groups are lower alkyl, which may be straight or branched chain, and which contain up to 10 carbon atoms. These groups include methyl, ethyl, propyl, isopropyl, butyl, isobutyl, tertiary butyl, secbutyl, amyl, hexyl, heptyl, octyl and the like. The preferred alkyl groups contain up to 5 carbon atoms. The especially preferred alkyl groups contain up to 3 carbon atoms. The most preferred is ethyl.

The term aryl refers to an aromatic group which contain up to 10 ring carbon atoms. This group includes phenyl, napthyl (alpha and beta). The most preferred aryl group is phenyl.

The aralkyl groups include, for example, benzyl, phenethyl, phenpropyl, phenbutyl, xylyl, p-diethylphenyl and the like.

Another preferred embodiment of the present invention contemplates substantially pure stereoisomer(s) of compounds having the formula:

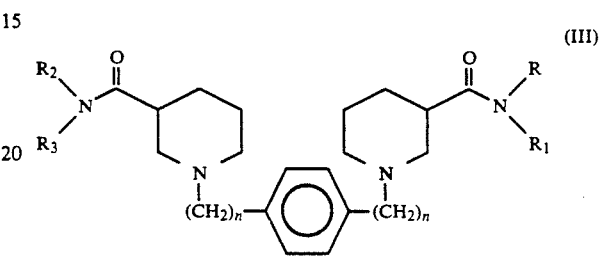

wherein n=1–5, and R, $R_1$, $R_2$ and $R_3$ are the same or different and are chosen from alkyl ($C_1$–$C_{10}$), aryl ($C_6$–$C_{10}$), aralkyl ($C_7$–$C_{12}$) or a heterocyclic group, or R and $R_1$ taken together with the nitrogen atom to which they are attached or $R_2$ and $R_3$ taken together with the nitrogen atom to which they are attached form a saturated 5- or 6-membered heterocyclic ring and addition salts thereof with pharmaceutically acceptable acids. In one embodiment, the present invention contemplates stereoisomers of compounds of General Formula (III) which exhibit, in the light absorbing region, a positive cotton effect in circular dichroic spectra. In a second embodiment, the present invention contemplates stereoisomers of compounds of General Formula (III) which exhibit, in the light absorbing region, negative cotton effect in circular dichroic spectra.

All of the stereoisomers of compounds of General Formula III are contemplated by the present invention. However, it is preferred that the compounds of the present invention be the (R,R) or (S,S) enantiomer.

A more preferred embodiment of the present invention contemplates substantially pure stereoisomers of compounds having the formula:

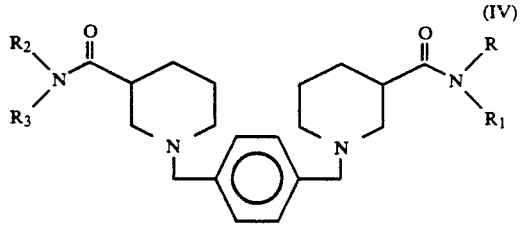

wherein R, $R_1$, $R_2$ and $R_3$ are the same or different and are chosen from alkyl ($C_1$–$C_{10}$), aryl ($C_6$–$C_{10}$), aralkyl ($C_7$–$C_{12}$) or a heterocyclic group, or R and R taken together with the nitrogen atom to which they are attached or $R_2$ and $R_3$ taken together with the nitrogen atom to which they are attached form a 5- or 6-membered saturated heterocyclic ring and addition salts thereof with pharmaceutically acceptable acids. In one embodiment, the present invention contemplates stereoisomers of compounds of General Formula (IV) which exhibit, in the light absorbing region, a positive cotton effect in circular dichroic spectra. In a second embodiment, the present invention contemplates stereoisomers of compounds of General Formula (IV) which exhibit, in the light absorbing region, a negative cotton effect in circular dichroic spectra.

All of the stereoisomers of compounds of General Formula (IV) are contemplated by the present invention. However, it is preferred that the compounds of the present invention be the (R,R) or (S,S) enantiomer.

In all the embodiments described hereinabove, it is preferred that R, $R_1$, $R_2$ and $R_3$ are alkyl groups, especially, alkyl groups having 1 to 5 carbon atoms, and most especially 1 to 3 carbon atoms. It is also preferred that R, $R_1$, $R_2$, and $R_3$ are aralkyl, especially wherein the aryl group is phenyl and the alkyl groups have 1-5 carbon atoms and most preferably 1-3 carbon atoms. Preferred aralkyl groups include phenpropyl, phenethyl and especially benzyl. Furthermore, it is also preferred that one of R and $R_1$ and one of $R_2$ and $R_3$ is alkyl and the other of R and $R_1$ and the other of $R_2$ and $R_3$ is aralkyl (e.g. benzyl). Moreover, it is preferred that when R, $R_1$, $R_2$ and $R_3$ contain alkyl or aralkyl, the alkyl group are straight chains. Furthermore, it is most preferred when $R=R_2$ and $R_1=R_3$. Another preferred embodiment is that when $R=R_2$ and $R_1=R_3$, R, $R_1$, $R_2$ and $R_3$ are lower alkyl having 1-5 carbons and more especially 1-3 carbon atoms.

Another preferred embodiment is when R and $R_1$ taken together with the nitrogen atom to which they are attached or when $R_2$ and $R_3$ taken together with the nitrogen atom to which they are attached form a 5 or 6 membered nitrogen ring. It is most preferred that the heterocyclic ring is completely saturated. In a most preferred embodiment of the type, it is preferred that both R and $R_1$ taken together and $R_2$ and $R_3$ taken together independently form a 5 or 6 membered heterocyclic ring. In a still more preferred embodiment, it is preferred that both heterocyclic rings are identical; the most preferred heterocyclic ring is piperidine or pyrrolidine.

It is most preferred in all the embodiments herein that X is aralkyl having 7 to 12 carbon atoms. The preferred X is a group of the formula:

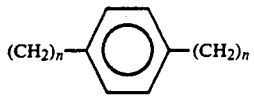

where each n is defined as 1, 2, 3, 4 or 5. It is preferred that each n is 1, defining p-xylyl.

In an embodiment of the present invention, the compounds of the present invention as depicted in Formulae II, IIa, III and IV are symmetrical, have a plane of symmetry passing through the X group. In other words, R, $R_1$, $R_2$ and $R_3$ have the same values. Moreover, the X group is preferably symmetrical in this embodiment. For example, in this embodiment, when the X is phenalkyl, the alkyl group is para-substituted on the phenyl ring. In the case where X is alkyl, it is preferred in this embodiment that X is a straight chain alkyl group as defined herein. Finally, X can also be unsubstituted phenyl or naphthyl.

The various combinations and permutations of the Markush groups of $R_1$, $R_2$, $R_3$ R, X and n described herein are contemplated to be within the scope of the present invention. Moreover, the present invention also encompasses compounds and compositions which contain one or more elements of each of the Markush groupings in $R_1$, $R_2$, $R_3$, n, X and R and the various combinations thereof. Thus, for example, the present invention contemplates that $R_1$ may be one or more of the substituents listed hereinabove in combination with any and all of the substituents of $R_2$, $R_3$ R and X with respect to each value of n.

Additional variations in the structural formulae above can be effected without significantly altering the therapeutic properties thereof. For example, the alkyl, aryl, aralkyl, or heterocyclic moieties can be substituted by one or more of a variety of substituents, such as hydroxy, halogen, alkyl and the like.

An inhibitor of human or animal blood platelet aggregation is racemic a-a'-Bis[3-(N,N-diethyl-carbamoyl)-piperidino]-p-xylene dihydrobromide (I), shown below.

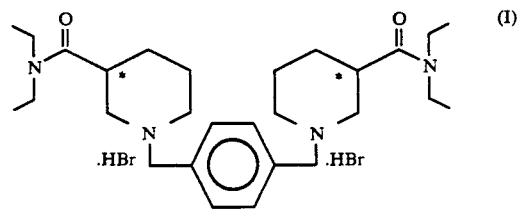

*indicates chiral center

Because of the presence of two chiral centers, Compound (I) is expected to exist in three configurations; R,R; S,S; and R,S (meso). Since Compound I is a symmetrically bis-substituted compound, R,S- and S,R-configurations are identical. Consequently I can exist in the following stereoisomeric forms:

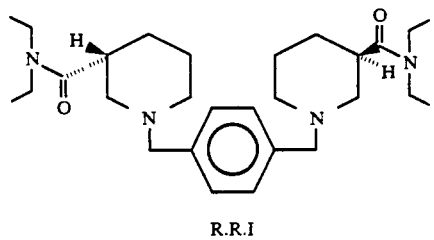

R.R.I

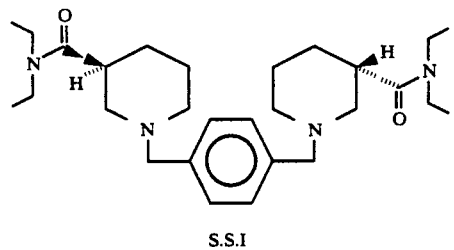

S.S.I

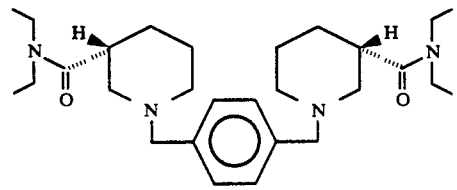

R,S(mono)-I

The (+) enantiomer of α,α'-Bis[3-(N,N-diethylcarbamoyl)piperidino]-p-xylene dihydrobormide (I), i.e., the enantiomer exhibiting a positive cotton effect in circular dichroic spectrum, demonstrates unexepectedly superior activity as a platelet aggregation inhibitor, as compared to racemic (I).

The compounds of the present invention can be prepared by art recognized techiniques. For example, these compounds can be prepared according to the procedures described in U.S. Pat. Nos. 4,634,709 and 4,657,917 both to Lasslo, et al. which are incorporated herein by reference. Furthermore, the following scheme is exemplary for the preparation of the compounds of the present invention.

Scheme I

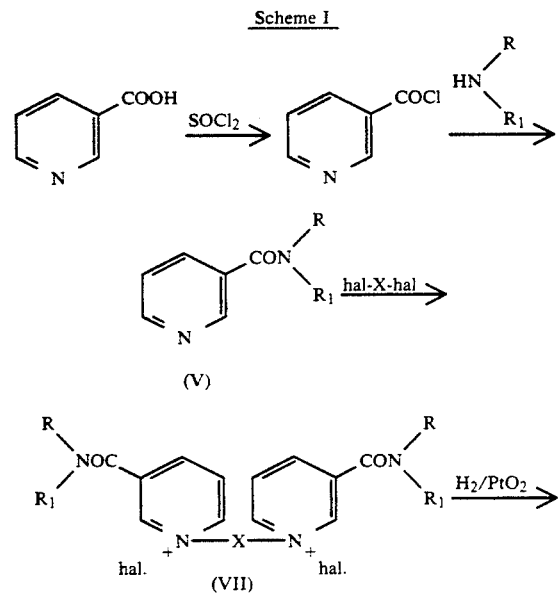

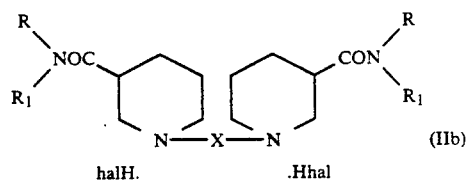

In the foregoing scheme, $R=R_2$ and $R_1=R_3$; all other substituents are as previously defined.

As depicted in Scheme I, nicotinoyl chloride is prepared by treating nicotinic acid with thionyl chloride at room temperature. Conversion into the corresponding amide is achieved by treating the nicotinoyl chloride with the appropriate secondary amine. Two moles of the amide (V) are refluxed with one mole of α,α'-dihaloalkane or α,α'-dihalo aralkane (VI) in a solvent (ethanol, acetone, etc.) and refluxed until the quarternary compound separates out as an insoluble precipitate (VII). The precipitated quaternary compound is purified by recrystallization, and then is dissolved in water or water/ethanol and reduced with $H_2/PtO_2$ at room temperature until hydrogen uptake ceases. Sometimes a higher temperature (55° C.) has to be employed. The solvent is evaporated under reduced pressure and the resultant α,α'-bis[3-(N,N-dialkylcarbamoyl)piperidino-]alkane or aralkane dihydrohalide (IIb) is purified by recrystallization from an appropriate solvent.

When Compound II is di-substituted, the following Scheme II is exemplary for their preparation.

Scheme II

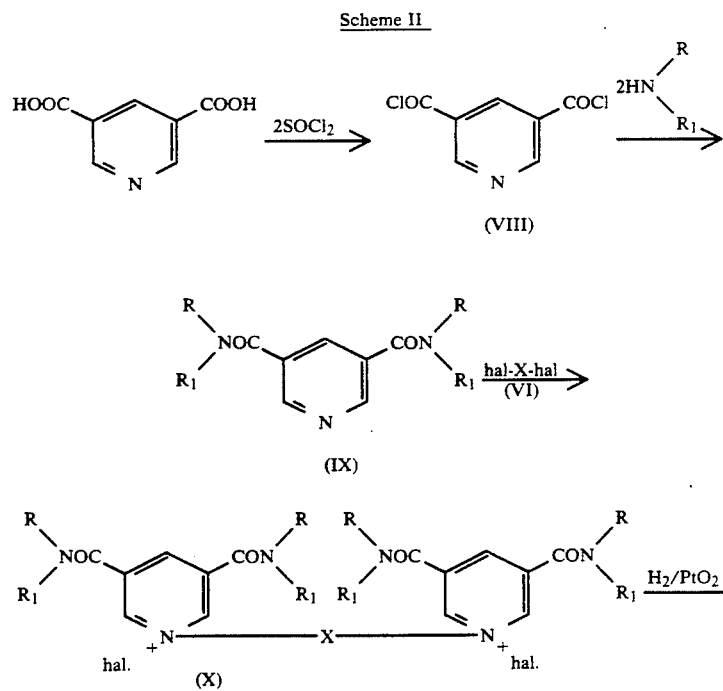

Scheme II

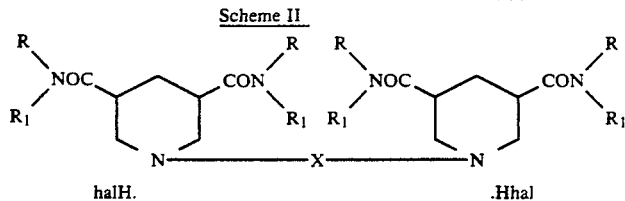

In the foregoing scheme, $R=R_2$ and $R_1=R_3$. The procedure of Scheme II is similar to that of Scheme I. Briefly, 3-5-di-nicotinoylchloride (VIII) is prepared by treating pyridine 3,5-di-carboxylic acid with thionyl chloride at room temperature. Conversion into the corresponding amide is achieved by treating the 3,5-dinicotinoylchloride (VIII) with the appropriate secondary amine. Two moles of the 3,5 di-amide (IX) are refluxed with one mole of $\alpha,\alpha'$-dihaloalkane or $\alpha,\alpha'$-dihalo aralkane (VI) until the quaternary compound separates out as an insoluble precipitate (X). The quaternary compound is then hydrogenated in accordance with Scheme I.

Using the methodology described hereinabove, the compound of Formula II is formed as a racemate. It consists of two pairs of diastereomers consisting of the two enantiomers. For example, the (R,R) and (S,S) as one diastereomeric pair and the (R,S) and (S,R) as the other pair. (Of course it is to be noted that when R, $R_1$, $R_2$ and $R_3$ have the same value, then the meso compound would be formed). The diastereomeric pair can be separated into its enantiomeric pair by techniques known to one skilled in the art, e.g., fractional recrystallization column chromatography and HPLC. Thus, by the conventional techniques, the enantiomeric pair containing the (R,R) and (S,S) will be separated from the enantiomeric pair containing the (S,R) and (R,S) forms.

The racemate consisting of the enantiomeric pair of Formula II can be separated into its separate enantiomers by art recognized techniques using chiral reagents or chiral chromatographic techniques known to one of ordinary skill in the art. For example, the racemic mixtures of the compounds of Formula II can be reacted with an optically active compound, e.g., a chiral acid, such as D(−)- or L(+)-tartaric acid, dibenzoyl-L(+)-tartaric acid, dibenzoyl-D-(−)-tartaric acid, and R(−)- or S(+)-mandelic acid, to form diastereomeric salts. The diastereomers can then be separated by recognized techniques known in the art, such as fractional recrystallization, column chromatography, HPLC and the like. Alternatively, these compounds can be separated by using chiral chromatographic techniques such as chiral HPLC, in which the stationary phase is a chiral compound, e.g., $\alpha_1$-acid glycoprotein (AGP), NEC $\beta$-cyclodextrin, (R)-naphthylalanine, (S)-naphthylleucine, (R)-naphthylurea, and (R)-(3,5-dinitrobenzoyl)-phenylglycine, and the like.

An exemplary procedure for the preparation and resolution of compounds of the present invention is described hereinbelow, i.e., a procedure for obtaining the (+) enantiomer of $\alpha\text{-}\alpha'$-Bis(3-N,N-diethylcarbamoyl)piperidino]-p-xylene dihydrobromide (I).

Compound (I), like many other drugs, exhibits stereoisomerism. Since these drugs interact with phospholipid molecules which contain many chiral centers, the present inventors explored the enantioselective activity of (I) and found, unexpectedly that the (+) enantiomer possesses most of the therapeutic activity.

Synthesis of Racemic $\alpha\text{-}\alpha'$-bis[3-(N,N-diethylcarbamoyl)piperidino-p-xylene dihydrobromide (I)

Racemic (I) was synthesized as described by Quintana, et al. [J. Pharm. Sci. Vol. 54, Pages 785–787 (1965)] which is specifically incorporated herein by reference. Briefly, $\alpha,\alpha'$-dibromo-p-xylene (30.0 g, 0.1136 mole) in 400 ml acetone was added to a solution of N,N-diethylnicotinamide (41.93 g, 0.2353 mole) in 700 ml absolute ethanol and refluxed (8.5 h) to yield $\alpha,\alpha'$-bis[3-(N,N-diethylcarbamoyl)pyridinium]-p-xylene dihydrobromide (36.3 g, 0.0585 mole, mp 267.4°–268.1° C.). Hydrogenation (PtO$_2$,/H$_2$, 50 psi) of the quaternary compound (25.0 g, 0.0403 mole) afforded I.2HBr (25.0 g, 0.0395 mole). The crude product (25.0 g) was dissolved in hot absolute ethanol and allowed to cool to room temperature. After three days, the separated crystals were filtered off to yield 9.4 g (0.0149 mole) of the "first crop", mp 280°–281° C. (decomp). The mother liquor, upon standing for 7–10 days afforded 6.5 g (0.0103 mole) of the "second crop", mp 279.0°–279.8° C. (decomp).

Resolution of Racemic (I)

Because of the presence of two chiral centers, Compound (I) exists in three configurations; the S,S, enantiomer; the R,R enantiomer; and the [R,S (meso)] forms, represented below. Since the R,S- and S,R- forms are superimposable, and therefore archiral, they are represented as the meso configuration.

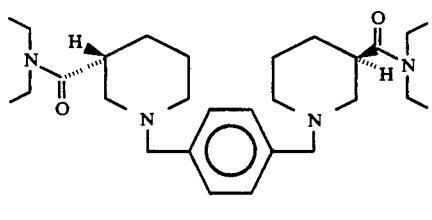

R.R.I

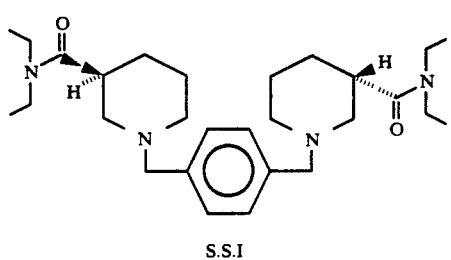

S.S.I

-continued

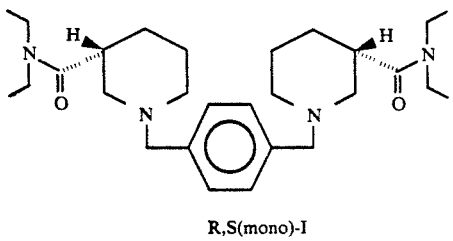

R,S(mono)-I

The preparative resolution of I into three stereoisomers is shown in Scheme 3.

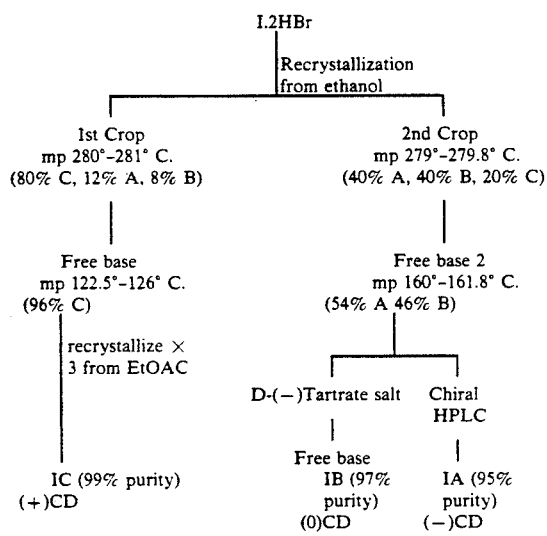

Scheme 3
Preparative Resolution of I

Recrystallization of the crude racemic I.2HBr afforded two crops of crystals from which low and high melting forms of the free base were obtained. More particularly, recrystallization of I.2HBr from absolute ethanol gave 9.4 g (0.0149 mole) of the "first crop", m.p. 280°-281° C. (decomp.). The filtrate yielded 6.5 g (0.0103 mole) of a "second crop", m.p. 279.8° C. (decomp.). This selective recrystallization was reproducible, with the three isomers crystallizing out in approximately the same ratios.

A solution of I.2HBr "first crop" (8.2 g) in water was adjusted to pH 9.0 with 29% $Na_2CO_3$ and then was shaken with ether, the extract evaporated and the residue was recrystallized from 15 ml ethyl acetate to yield 4.0 g I, mp 122.5°-126° C. (free base 1). Calc. for $C_{28}H_{46}N_4O_2$: C, 71.45%; H, 9.85%; N, 11.90%. Found: C, 71.47%; H, 9.48%; N, 11.92%. Isomeric purity by HPLC was 96% peak C. This was further purified by dissolving 2.5 g in boiling EtOAc (12.0 ml) and bringing it slowly to room temperature. After two days, the separated precipitate was recrystallized a third time from EtOAc to obtain 0.1 g of peak C of 99% isomeric purity by HPLC (FIG. 1). FIG. 1 is a chromatograph showing the purity of IC (0.5 mg injected) obtained by the fractional crystallization of I free base 1 on Chira-1AGP semipreparative column, 150×10 mm (5 μm) with diol precolumn 10 mm×10 mm (5 μm). Mobile phase was 0.025 M PB (pH 6.5) containing 0.025M TBA $HSO_4$, at a flow rate of 3.6 ml/min.

Figure 2:
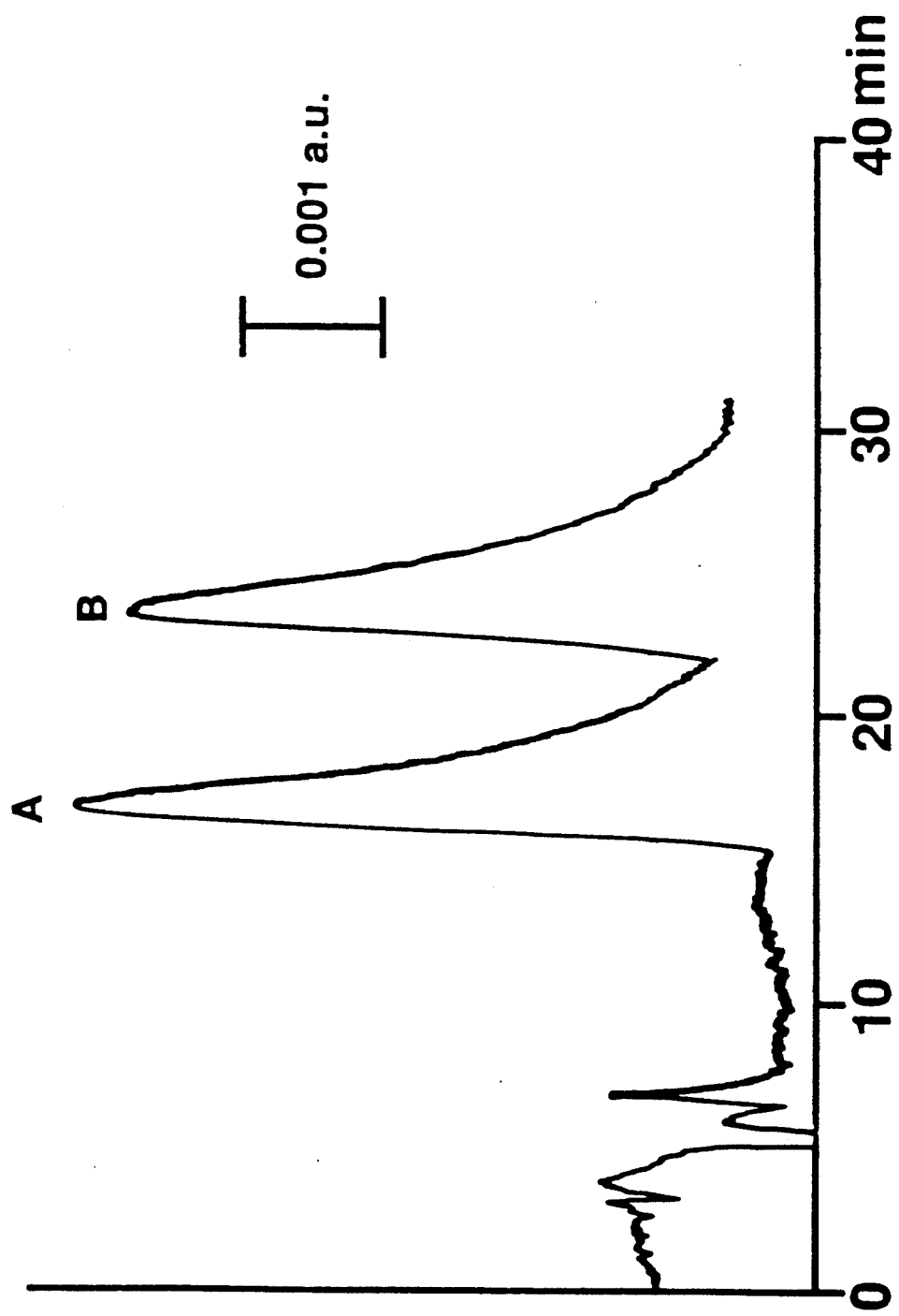
FIG. 2 is an HPLC showing the composition of I free base 2 (2.7 μg injected). A chiral-AGP analytical column, 100 mm×4 mm (5 μm) was used with a mobile phase consisting of 0.025M PB (pH 6.5) containing 0.025 M TBA HSO₄, at a flow rate of 0.4 ml.min.

Similarly, a solution of the "second crop" of the IHBr (31.6 g), in aqueous $NA_2CO_3$ was extracted with ether, and the free base recrystallized once from 140 ml EtOAc to give 10.9 g of I, mp 160°-161.8° C. (free base 2). Calc. for $C_{28}H_{46}N_4O_2$: C, 71.45%; H, 9.85%; N, 11.90%. Found: C, 71.50%; H, 9.62%; n, 11.73%. Isomeric purity by HPLC, 54% peak A, and 46% peak B (FIG. 2). FIG. 2 is a chromatograph showing the composition of I free base 2 with the conditions being the same as those employed in FIG. 1 (2.7 μg injected).

PHYSICAL CHARACTERISTICS OF THE COMPOUNDS AND THEIR FRACTIONS

Figure 3:
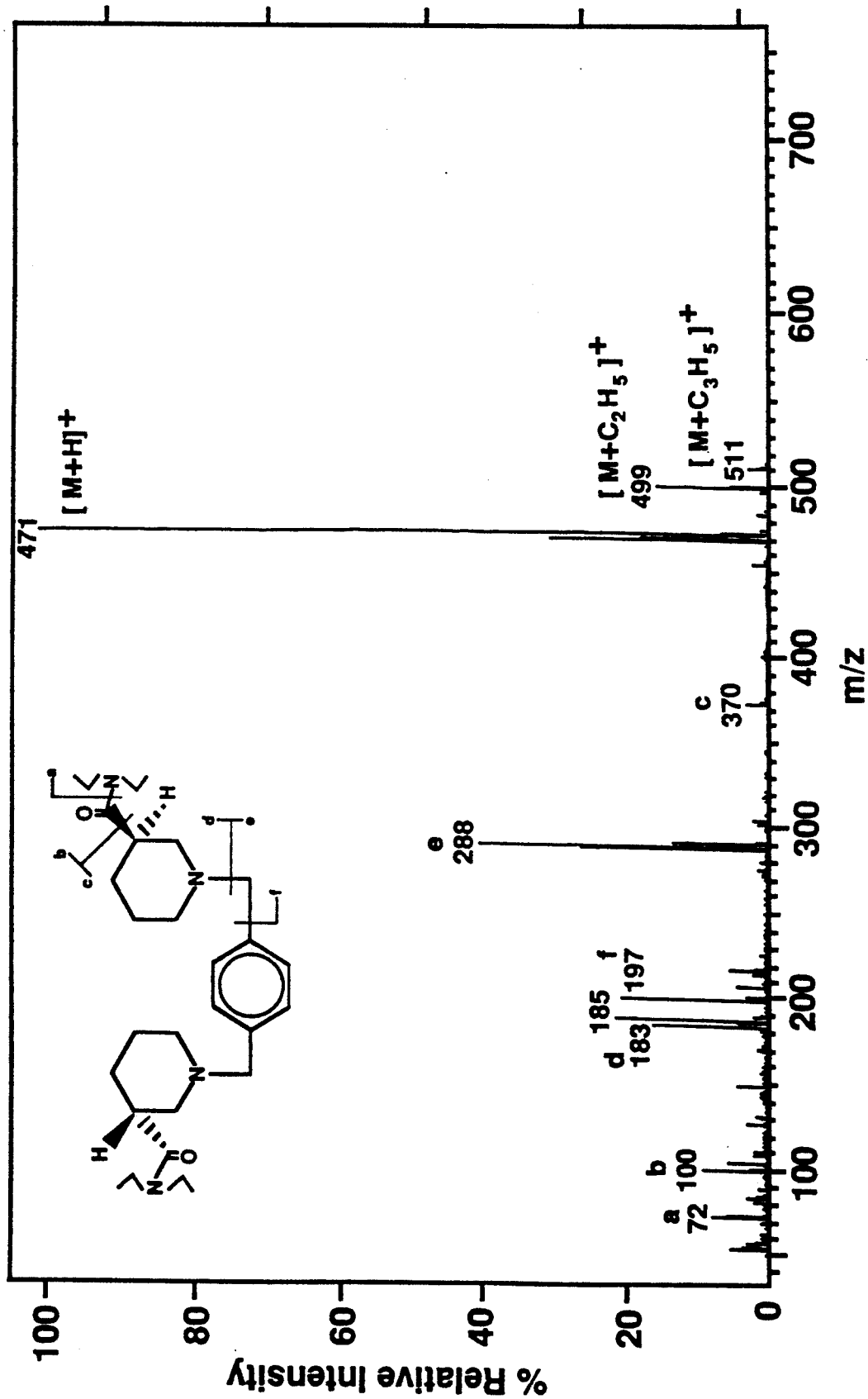
FIG. 3 is a methane DCI mass spectrum of free base 1, showing the proposed identities of the major mass fragment ions.
Figure 4:
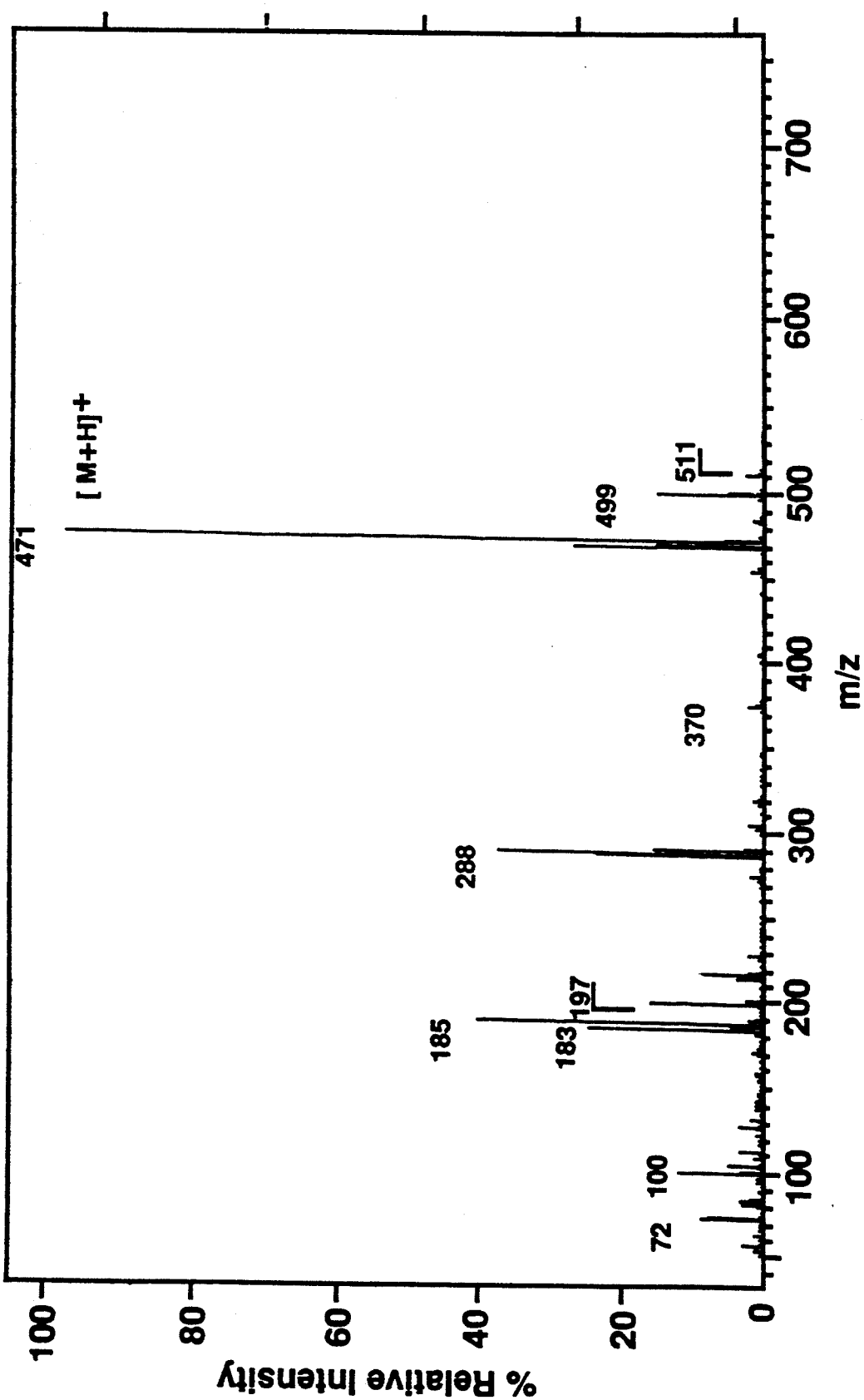
FIG. 4 is the methane DCI mass spectrum of free base 2.

The identity of the free bases 1 and 2 as having structure I was confirmed by elemental analysis and mass spectrometry. The mass spectrum of the (low melting) free base 1 gave a strong $[mH]^+$ ion at m/2 471.5 and was consistent with the proposed structure (FIG. 3). Similarly the (high melting) free base 2 gave a strong $[mH]^+$ ion at 471 (FIG. 4) and the mass spectrum was identical with that of the former, suggesting that both forms of the free base are positional isomers. (Mass spectra were recorded on a Finnigan MAT, TSQ-70 triple quadruple ms spectrometer in the positive ion methane desorption chemical ionization mode).

Figure 5:
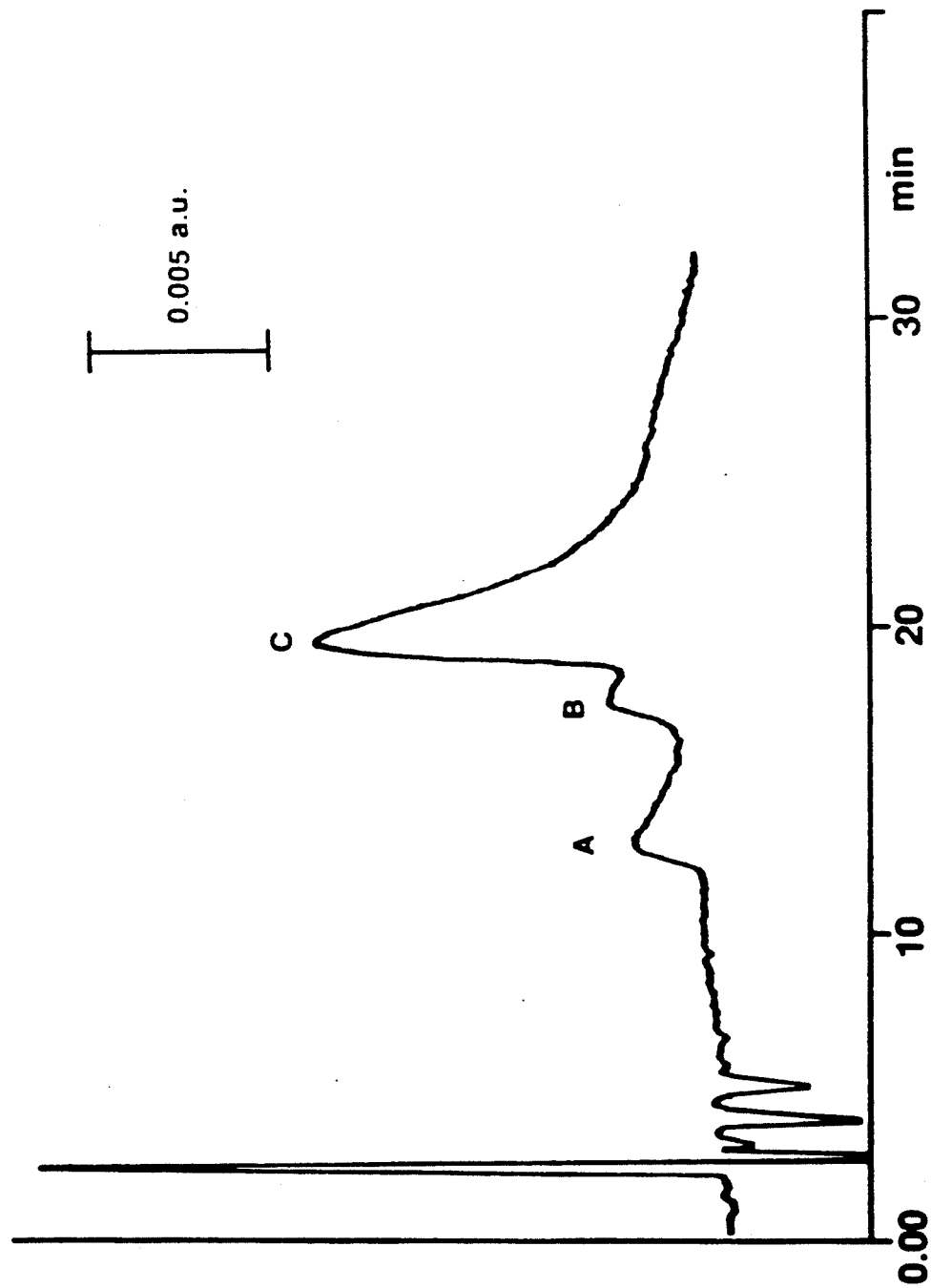
FIG. 5 is a chromatogram showing resolution of I.2HBr, first crop (2.0 μg injected). Conditions are the same as those employed in FIG. 2.
Figure 6:
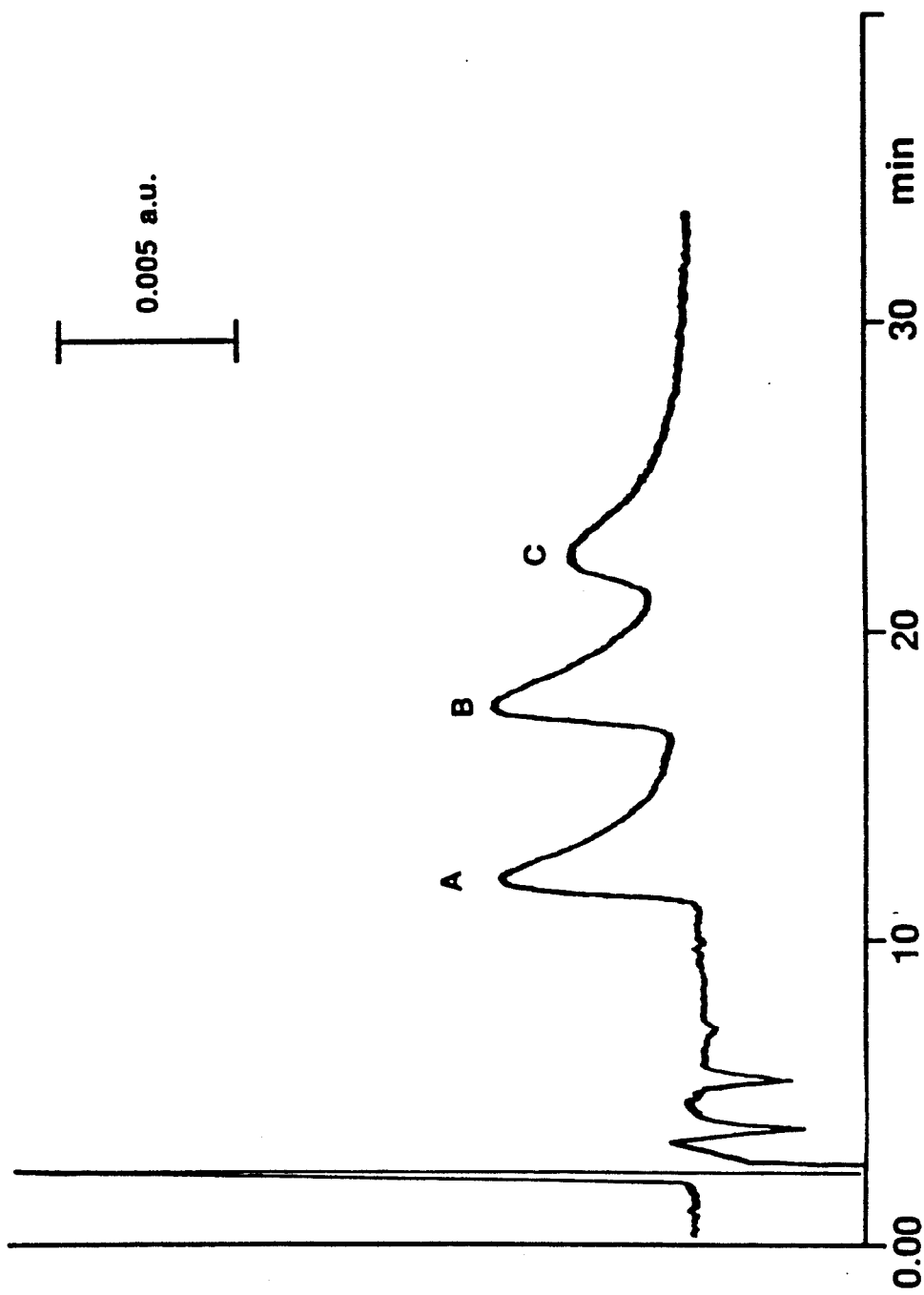
FIG. 6 depicts the chromatographic resolution of I.2HBr, second crop (2.0 μg injected). Conditions same as those described in FIG. 2.

Synthetic I 2HBr (first crop) was resolved into 3 peaks, IA, IB and IC in an approximate ratio of 12:8:80, on a chiral $\alpha_1$-acid glycoprotein column. More particularly, a chiral-AGP analytical column, 100 mm×4 mm (5 μm) was used with a mobile phase consisting of 0.025 M phosphate buffer (PB) (pH 6.5) containing 0.025 M tetrabutylammonium hydrogen sulfate ($TBA.HSO_4$), at a flow rate of 0.4 ml/min. FIG. 5 shows the chromatographic resolution of the first crop of (I).-2HBr (2.0 μg injected) Similarly, resolution of the second crop of I.2HBr afforded isomers A, B and C in a ratio of 40:40:20 (FIG. 6).

Figure 7:
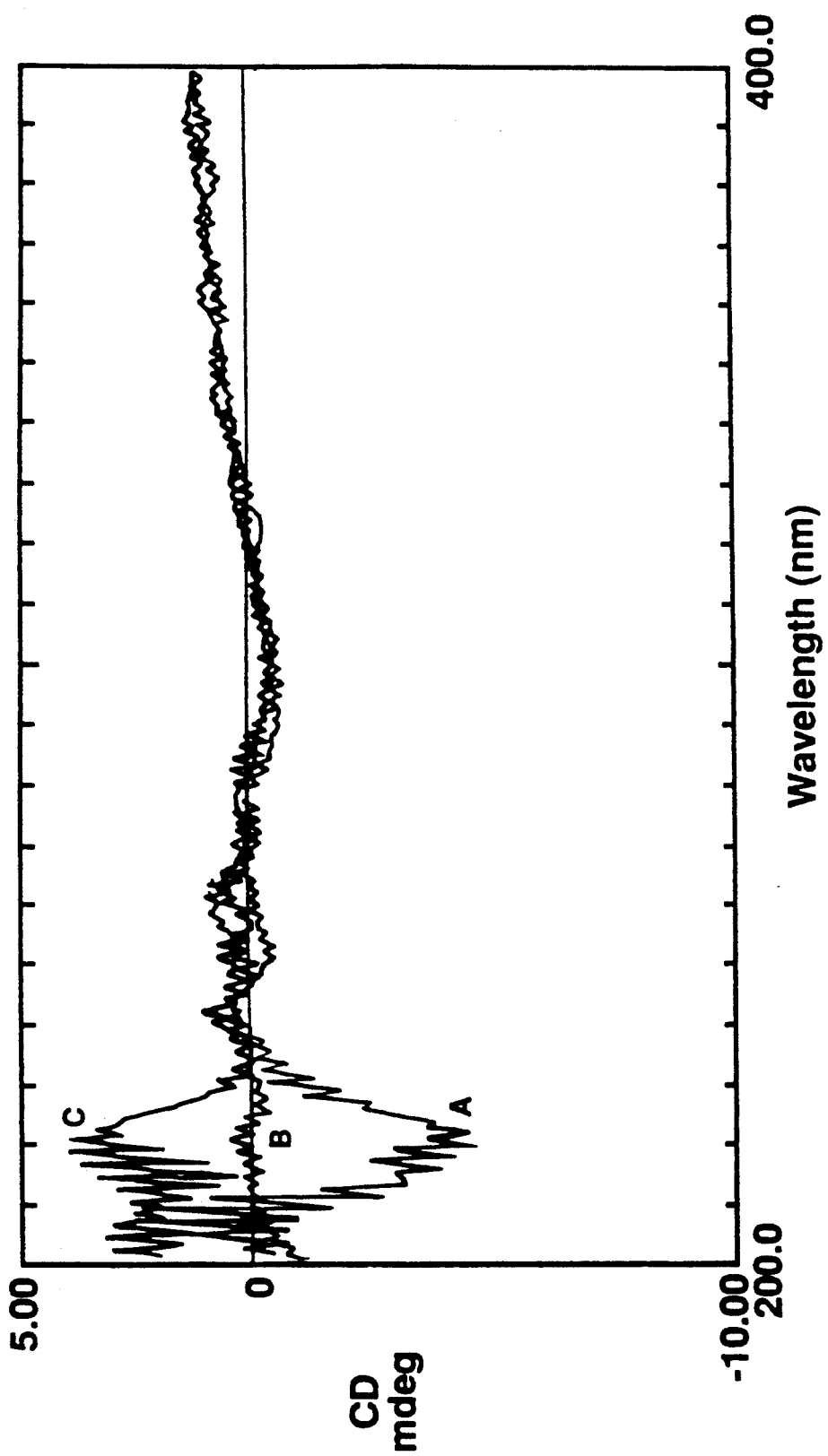
FIG. 7 shows the circular dichrograms of I A, B and C.

It is apparent from the circular dichroic (CD) spectra of the three isomers thus resolved, that IA has a negative CD cotton effect at 220 nm and that IC has a positive CD cotton effect at the same wavelength (FIG. 7). Thus, the two are enantiomers. IB appears to be the meso isomer with no CD cotton effect. Circular dichroic spectra were obtained in a Jasco 500 spectropolarimeter using compound solutions (approximately 1.0 μg/ml) in 0.5 mM PB (pH 6.5) containing 0.5 mM $TBA.HSO_4$.

Table I, below, summarizes the organic microanalysis data compiled with respect to free base 1 and free base 2.

TABLE 1

| | | | ORGANIC MICROANALYSIS DATA | | | | | |
|---|---|---|---|---|---|---|---|---|
| | | | Anal. (%) | | | | | |
| | | | Calcd. | | | Found | | |
| Compound | m.p. (°C.) | Formula | C | H | N | C | H | N |
| Free base 1 | 122.5–126.0 | $C_{28}H_{46}N_4O_2$ | 71.45 | 9.85 | 11.90 | 71.47 | 9.48 | 11.92 |
| Free base 2 | 160.0–161.8 | $C_{28}H_{46}N_4O_2$ | 71.45 | 9.85 | 11.90 | 71.50 | 9.62 | 11.73 |

Microanalyses were performed by Galbraith Laboratories Inc., Knoxville, TN

Chiral Resolution

Figure 8:
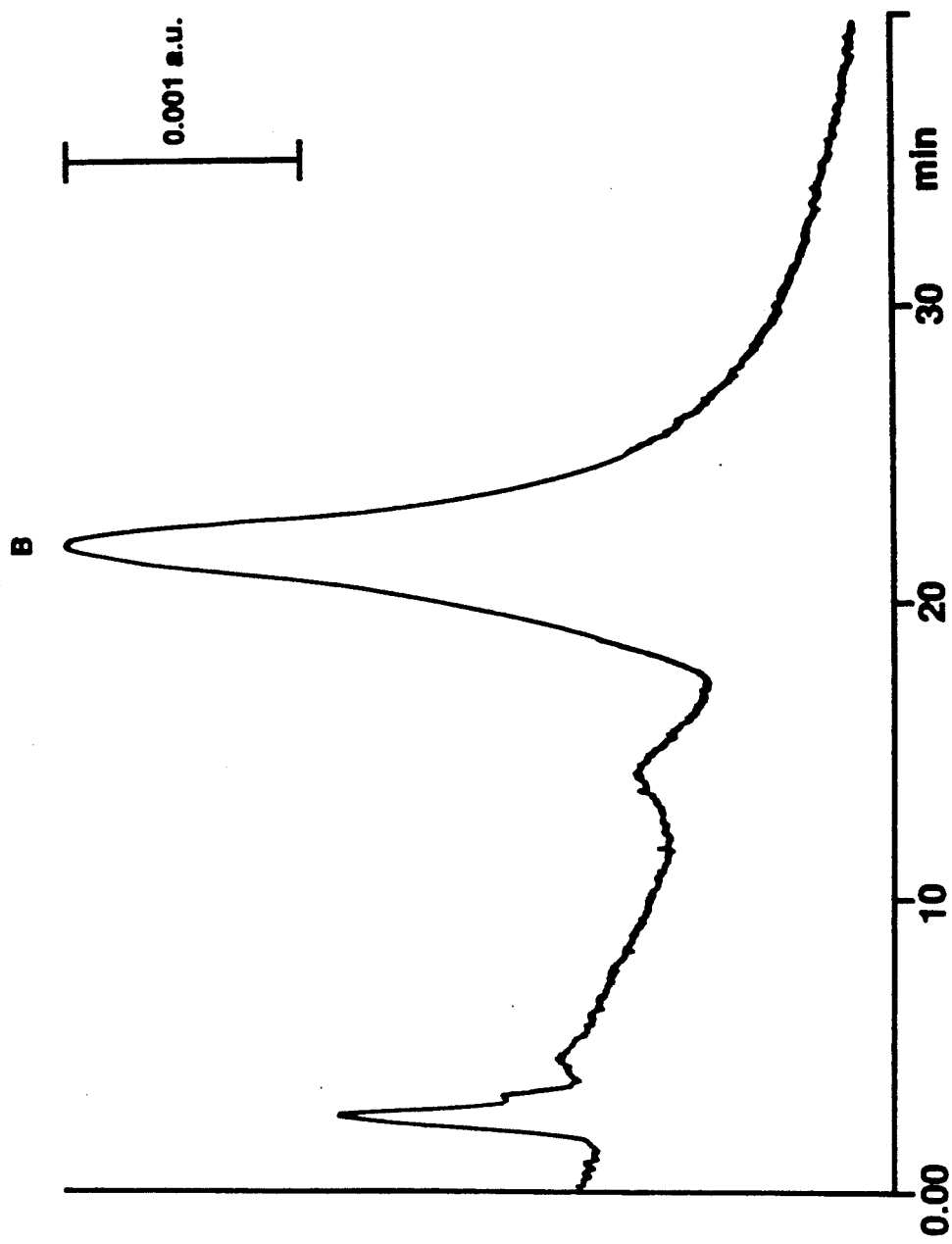
FIG. 8 is a chromatogram showing the purity of IB obtained through diastereomeric D—(—)tartrate formation (conditions same as in FIG. 1, 0.5 mg injected).

Diastereomeric tartrate formation. The free base 2 (3.0 g, 0.00637 mole) and D-(−)-tartaric acid (1.92 g, 0.0128 mole) were dissolved in 50 ml of warm absolute ethanol and kept at room temperature for three days. The precipitate was recrystallized from aqueous 91% ethanol. The resulting I.D-(−) tartrate was dissolved in 1.0 ml water, made alkaline (pH 9.0) with aqueous 29% $Na_2CO_3$ and the mixture extracted three times with ether. The combined ether layers were washed repeatedly with water and evaporated under reduced pressure. The resulting solid was recrystallized from ethyl acetate to give 8.9 mg of peak B. Isomeric purity of Peak B by HPLC was 97% (FIG. 8). The purity of IB (0.5 mg injected), depicted in FIG. 8, was obtained by the chromatographic resolution of I free base 2 on chiral-AGP semipreparative column, 150×10 mm (μm). Mobile phase was 0.025 M PB (pH 6.5) containing 0.025 M $TBA.HSO_4$, at a flow rate of 3.6 ml/min. The chromatographic system consisted of a Water U6K injector, a model 600E Powerline multisolvent delivery system, a model 484 tunable UV/VIS detector, a NEC PowerMate SX plus computer and a NEC P5200 printer/plotter. A chiral-AGP ($a_1$, acid glycoprotein) analytical column 100×4.0 mm (5 μm) and a chiral-AGP semipreparative column 150×10.0 mm (5 μm) (ChromTech AB, Norsborg, Sweden) attached to a diol precolumn, 10×10 mm (5 μm) were purchased from Regis Chemical Company, Morton Grove, Ill.).

Resolution of I on chiral-AGP column. The mobile phase consisted of 0.025 M phosphate buffer (PB), pH 6.50 containing 0.025 M tetrabutylammonium (TBA) hydrogen sulfate. The flow rate was 0.4 ml/min with the analytical column and 3.6 ml/min with the semipreparative column.

Figure 9:
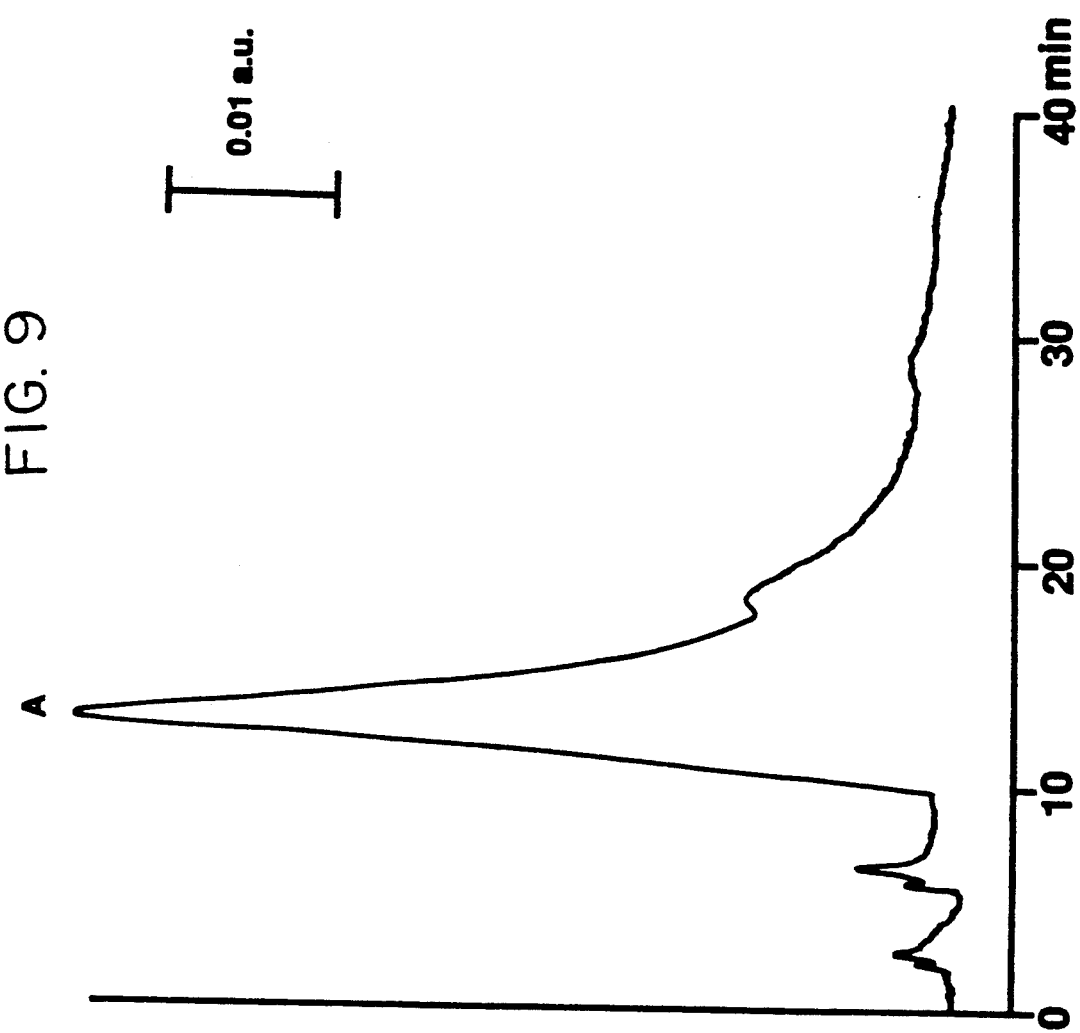
FIG. 9 depicts the purity of IA (0.5 mg injected) obtained by the chromatographic resolution of I free base 2 on chiral-AGP semipreparative column. Conditions the same as those employed in FIG. 1.

Preparative HPLC. A 80 μl aliquot of a solution (10 mg/ml) of the free base 2 in the HPLC mobile phase was injected into the semipreparative chiral-AGP column, and the eluant corresponding to peak A was collected. This was repeated until 115 mg of the free base was resolved. The resulting eluant (2.5 liter) was concentrated on a Rotavapor to 100 ml. The pH was adjusted to 9.0 with aqueous 29% $Na_2CO_3$ and the compound extracted four times with 200 ml portions of ether per extraction. The ether layer was washed three times with water and then dried over anhydrous $MgSO_4$. The solvent was evaporated under reduced pressure. The residue was stored at 5° C. for four days under N, and the resulting semisolid was recrystallized with EtOAc to yield 19.15 mg of peak A with 95% isomeric purity (FIG. 9). FIG. 9 shows the purity of peak A obtained by chromatographic resolution of I free base 2 on a chiral-AGP semipreparative column with the conditions being the same as those employed in FIG. 8.

Procedure for Determining In Vitro Platelet Aggregation-Inhibitory Activity. Adenosine diphosphate (ADP) was used to induce platelet aggregation and was utilized as the sodium salt. A 10 mM stock solution was prepared fresh before each use in modified Tyrode's buffer and working dilutions were prepared with modified Tyrode's buffer immediately prior to use. The buffer contained NaCl (137.00 mM), KCl (2.70 mM), $NaHCO_3$ (11.90 mM), $NaH_2PO_4H_2O$ (0.36 mM) and glucose (5.60 mM) in redistilled water. Adjustment to pH 7.4 was effected by addition of 1N HCl.

Venous blood for the examples set forth below was collected in plastic syringes from five health male volunteers (aged 18-35) who had fasted overnight and had abstained from all medications, alcohol, tobacco and caffeine for a period of at least one week prior to donations. The blood was transferred into plastic centrifuge tubes containing 3.2% sodium citrate (blood/citrate ratio 8:1) and centrifuged at 120Xg for 15 minutes at 23° C., yielding platelet-rich plasma (PRP); platelet-poor-plasma (PPP) was obtained by centrifugation of citrated whole blood at 1,100Xg for 15 min at 23° C. The platelet count of PRP was determined and adjusted to a final count of 300,000 platelet per $mm^3$ by dilution with autologous PPP. (Occasionally, blood from a given donor yielded PRP with a count lower than the stipulated figure; however, this was usually greater than 285,000, and never less than 250,000 platelets per $mm^3$). The plasma so obtained was transferred using a 1.0 ml Centaur pipette into a 50 ml polyethylene centrifuge tube. In order to maintain plasma pH in the appropriate range, the air in the tubes are displaced gently (2 minutes) with a 5% ($CO_2$-95% air (v/v) mixture and the tube capped. The plasma was maintained at 37° C. in a water bath until used in the aggregation experiments.

Assays of platelet aggregation were performed at least in duplicate, using plasma acquired from different donors, employing a method developed by Quintana, et al. (Quintana, et al., Relationships Between the Chemical Constitution of Carbamoylpiperidines and Related Compounds, and Their Inhibition of ADP-Induced Human Blood Platelet Aggregation, Thromb. Res. Vol. 22, Pages 665-680, 1981); Quintana, et al., Effects of Ethanol and of Other Factors on ADP-Induced Aggregation of Human Blood Platelets in Vitro, Thromb. Res., Vol. 20, Pages 405-415, 1980) (cf. Born, Nature, Vol. 194, Pages 927-929, 1962) and Mustard, et al., J. Lab. Clin. Med., Vol. 64, Pages 548-559, 1964).

Initially, in each experiment, 0.45-ml aliquots of PRP were placed in siliconized cuvettes and stirred (1,100 rpm) in the aggregometer at 37° C. to ascertain the absence of spontaneous aggregation. Appropriate ADP solutions (50 μl) were subsequently injected using a Hamilton microliter syringe to determine the minimal concentration eliciting maximal biphasic aggregation. This ranged from 3 μM to 10 μM but most frequently 7 μM. In each case, the concentration of ADP so determined was used in eliciting aggregation throughout each specific set of aggregometric evaluations.

0.5 μl of a solution of the evaluant compound in redistilled 95% ethanol was injected into a stirred (1,000 rpm) 0.4-ml aliquot of plasma in a siliconized cuvette in the aggregometer-well (37° C). After 15 seconds, the cuvette was transferred to an incubator (also at 37° C.) and the contents held at this temperature, without stirring, until 2 minutes postinjection. The cuvette was then returned to the aggregometer-well, a base-line being recorded for 2 minutes to detect any spontaneous aggregation. At exactly 4 minutes after injection of the evaluant solution, 50 μl of the appropriate ADP solution was injected and aggregation recorded for 5.5 minutes. Evaluants were studied at least 4 different concentrations. Control experiments (ethanol in a final concentration of 0.095% v/v) were performed in conditions parallel with those involving the respective evaluants, and were initiated either 1 minute prior to or 1 minute after the start of experiments employing the test compounds. This permitted injections to be made precisely at the specified times. Normally, 4 pairs (treated and control)

of aggregations were carried out at 10 minute internals beginning at 60 minutes post-veripuncture. Evaluant and control aggregations were tudied in alternate ($Y_1$ or $Y_2$) channels of the dual-channel aggregometer in order to detect any effects due to malfunction of a specific channel.

In evaluating aqqegometric tracings, primary attention was paid to intensity of aggregation, i.e., the maximum change in percentage of light transmittance with special attention to any abolition or diminution of the secondary and even the primary aggregation-waves. (Roper, et al., Am. J. Clin. Pathol., Vol. 71, Pages 263-268, 1979); Mills, et al., Life Sci., Vol. 14, Pages 659, 672, 1974); Newhouse and Clark, in Triplett (ed.), Platelet Function: Laboratory Evaluation and Clinical Application. Chicago, American Society of Clinical Pathologists, 1978, Pages 109-121). The concentration effecting 50% inhibition ($Ia_{50}$) was determined by linear regression analysis and the average $Ia_5$) of at least 5 values was calculated. Compounds with known antiplatelet activity (propranolol, trifluoperazine and chlorpromazine) were also included for comparisons.

Aggregation Inhibitory Activity

Table II shows the in vitro inhibitory activities of rac-I and its stereoisomers on human platelet aggregation induced by adenosine diphosphate (ADP). The (+)-isomer was most potent, being 15 times more active than its (−)-antipode and three times more potent than rac-I, suggesting a high degree of stereoselectivity in its interaction with chiral sites in the platelet.

TABLE II

| Inhibition of Human Blood Platelet Aggregation by rac-I and its Stereoisomers | |
|---|---|
| Compound | $Ia_{50}*(\mu M) \pm$ S.E. |
| rac-I.2HBr | 44.5 ± 127 |
| (−)-I (IA) | 233.4 ± 52.1 |
| (0)-I (IB) | 41.4 ± 11.8 |
| (+)-I (IC) | 15.3 ± 3.9 |
| Propranolol | 174.8 ± 17.0 |
| Trifluoperazine | 201.8 ± 21.9 |
| Chlorpromazine | 155.7 ± 25.5 |

*Compound concentrations affecting 50% inhibition of aggregation. n = 5 for (0)-I and 6 for all others.

Hypothetically, it appears that there is positive interaction with complementary chiral sites in the phosphatidylserine (PS) and phosphatidylinosito (PI) of the platelet membrane and/or membranes of platelet organelles. Preliminary modeling studies were recently conducted by the inventors using ALCHEMY II by Tripos. Each isomer of I and each fragment of the glycerophospholipid (sn-2-s-) was constructed, minimized and saved. The following three atom pairs were selected for interaction between each isomer and PS and PI: piperidino N, amide O, and, the α-C of one ethyl group on the amide N of I were paired respectively with the ionized 0 of the phosphate group, hydroxy group of the inositol moiety, and the α-C of the fatty acid side chain belonging to PI. Likewise, a similar pairing was made with PS. The FIT program, which calculates the root mean square value of one pair of structures, was used for each pair of isomer-PI and isomer-PS. The preliminary results consistently showed the best fit with the R,R enantiomer of I with both PI and PS. Similarly, the worst fit was found for S,S-I with both PI and PS. As expected, the R,S form was found to have an intermediate fit with PI and PS.

To confirm the preliminary results, a more detailed molecular modelling study was performed using the software package SYBYL (version 5.4) implemented on an Evans and Sutherland PS 290 graphics terminal connected to a minicomputer from SUN microsystems.

The structure of I enantiomers and PI were taken from the fragment library of SYBYL. Original models of compounds were built with standard bond length and angles. The energy of each compound was then minimized using MAXIMIN 2 force field.

After minimization, the enantiomers of I were interacted with PI using dock option of SYBYL based on the ionic bond and hydrogen bond interaction. The intermolecular energy of interaction between a pair of molecules was minimized with MAXIMIN 2 force field. The figures were photographed directly from the screen.

Figure 10:
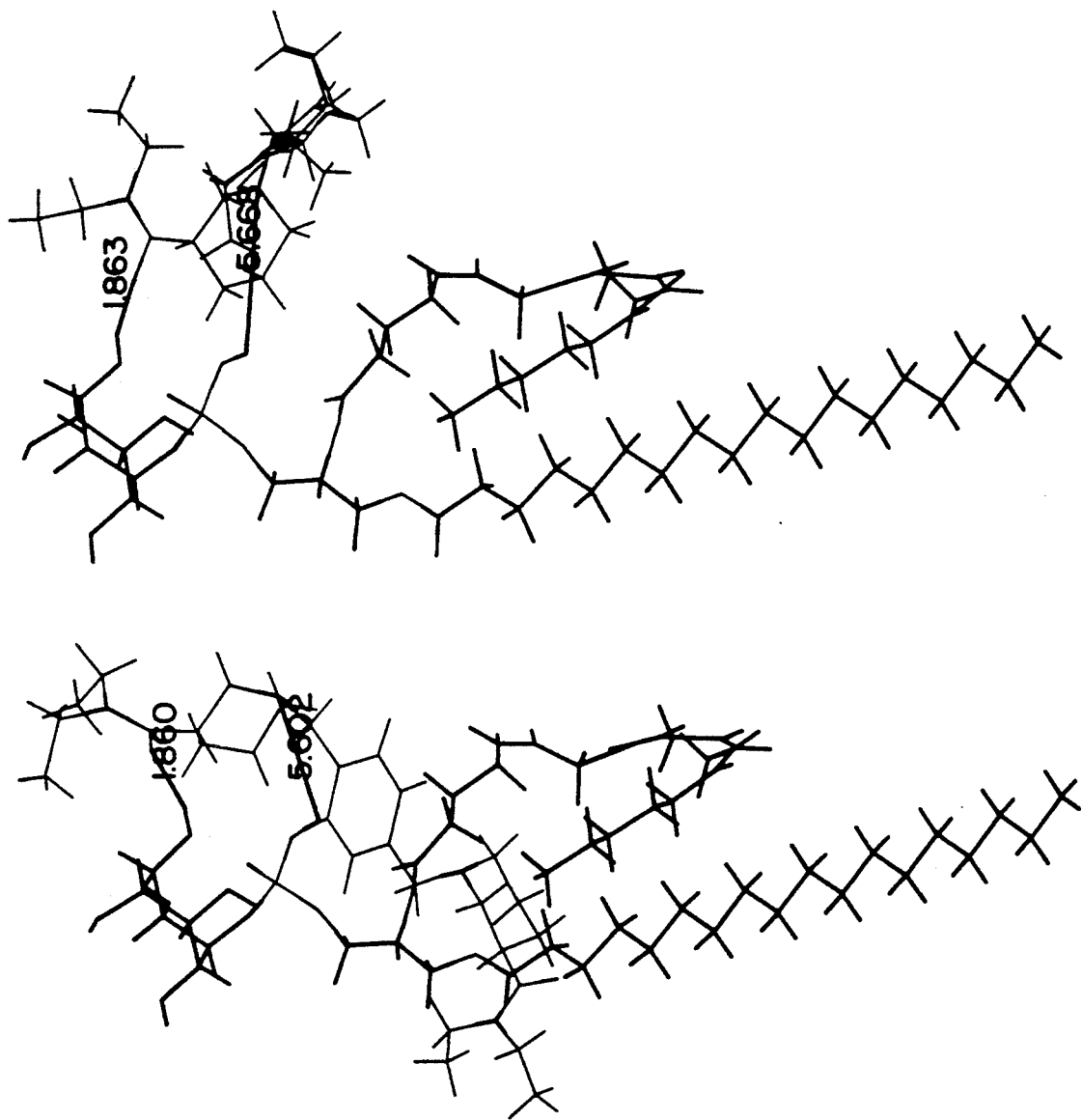
FIG. 10 is a molecular model depicting interaction between phosphatidylinositol and enantiomers of I. To the left is R,R—I. To the right is S,S—I. A hydrogen bond between the 3-OH group of inositol (of PI) and the amide O of I, and an ionic interaction between the phosphate oxygen of PI and the piperidinyl N of I, are depicted.
Figure 11:
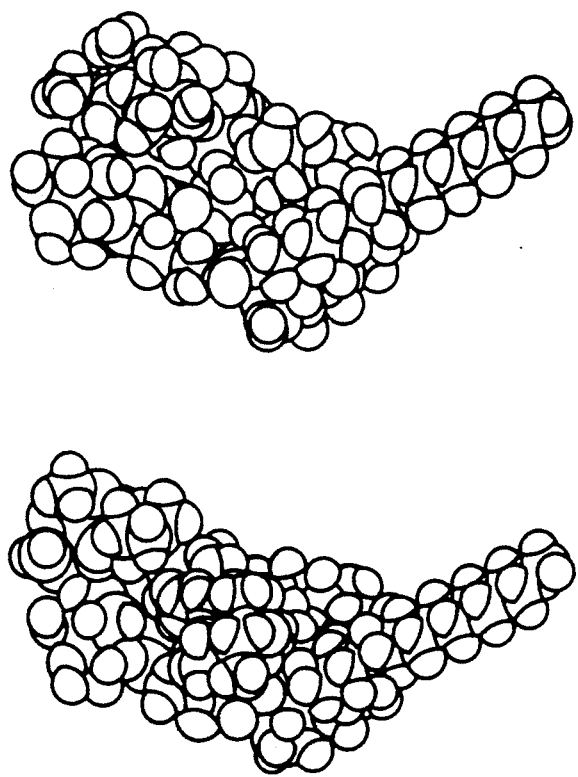
FIG. 11 is a space-filling molecular model depicting interaction between phosphatidylinositol and enantiomers of I. To the left is R,R—I and to the right is S,S—I. A hydrogen bond between the 3—OH group of inositol of PI and the amide 0 of I, and an ionic interaction between the phosphate oxygen of PI and piperidinyl N of I, are depicted. Both bonds are possible with R,R—I, for which the piperidinyl N is away from view. With S,S—I the ionic bond is not possible because the piperidinyl N is separated by other atoms, from the phosphate O.

The FIGS. 10 and 11 indicate that there is a better fit between the R,R enantiomer of I and PI than there is between the S,S enantiomer and PI.

FIG. 10 shows the stick model comparison between the complex pairs R,R enantiomer/PI and S,S enantiomer/PI. It is qualitatively clear that the R,R enantiomer fits better in the proposed active site region selected for PI. FIG. 11 shows the identical systems in FIG. 10 in space-filling representation. Furthermore, the energy of the R,R enantiomer/PI complex is 17 kcal/mole less than that for the S,S enantiomer/PI complex.

R,R-I interacts with PI (energy of interaction 44.3 kcal/mole) forming a hydrogen bond (between the amide oxygen of I and the 3-OH group of inositol in PI), and an ionic bond (between the piperidinyl N of I and the phosphate O of PI). The energy of interaction between PI and S,S-I is 61.9 kcal/mole. While in the latter case, hydrogen bond formation is possible, ionic bond is not possible inasmuch as the piperidinyl N of I is separated from the phosphate 0 of PI by other atoms (see FIG. 11, space-filing model).

Studies using x-ray crystallography are under way to determine the absolute configuration of the enantiomers. Until such time as the assignment is made, however, one can conclude that the R,R enantiomer binds better to the proposed binding site and, therefore, is predicted to be enantiomer C (I(+)). Although the absolute stereochemical conformations of the three isomer fractions of I is not presently known, I-A and I-C are enantiomers, and one of these should be R,R- and the other S,S- conformation. R,S-I is expected to be the meso diastereomer.

MOUSE ANTITHROMBOTIC ASSAY

The method employed is similar to Myers, et al's (Proc. Soc. Exp. Biol. Med., Vol. 183, Pages 86-91, 1986) modification of the procedure of DiMinno and Silver (J. Pharmacl. Exp. Therap., Vol. 225, Pages 57-60, 1983). Male ICR mice 25 g-35 g were used in this study. Collagenreagent Horm, containing 1 mg/ml of native collagen fibrils from equine tendons suspended in isotonic glucose solution of pH 2.7 was obtained from Horm -Chemie Momchem GMBH, Munchen, Germany; Epinephrine Injection, USP 1 mg/ml was from Abbott Laboratories, North Chicago, Ill.

Rac.I.2HBr was dissolved in physiological saline and (+)-I (I-C) was dissolved in saline at pH 6.5 at a concentration which yielded the desired dosage when 10 ml/kg of the compound solution was injected intraperitoneally (i.p.) to the mouse. Control mice received 10 ml/kg of the solvent/vehicle intraperitoneally.

Thirty (30) minutes after administration of test compound, the mouse was challenged with intravenous collagen-epinephrine suspension. The procedure is as follows: Fifteen (15) minutes after i.p. administration of test compound, the mouse was given 50-60 mg/kg of pentobarbital sodium (Nembutal). About 10-12 minutes later (when the mouse was anesthetized) the jugular vein was surgically exposed in preparation for the intravenous collagen-epinephrine injection.

Thirty (30) minutes after i.p. administration of the test compound (and about 15 minutes after i.p. Nembutal) the mouse's platelets were challenged with 0.00333 ml/gm (0.10 ml/30 gm mouse) of the intravenous collagen-epinephrine suspension into the jugular vein. [The collagen-epinephrine suspension contained 0.15 mg collagen fibrils and 0.018 mg of epinephrine per ml of the suspension]. The rate of injection for the collagen-epinephrine suspension was consistent from one mouse to the next.

The mouse was observed for immediate and delayed reactions to the collagen-epinephrine challenge. If the mouse died anytime within sixty (60) minutes following intravenous collagen-epinephrine, the mouse was scored as "dead", i.e., presumably was not protected by the test compound, whereas, if the mouse did not die within this 60 minute period, the mouse was scored as "lived", and presumably its platelets were "protected" from a fatal aggregation by the test compound.

Graded doses of the compound were administered to mice prior to the aggregation challenge. The ED50 was determined graphically from a Probit-log plot of percent of mice protected (Probit) by each dose (log scale) of the compound. The ED50 is the dose (on the log scale) where the straight line plot crosses the probit 5.0 (i.e., 50% protected).

Figure 12:
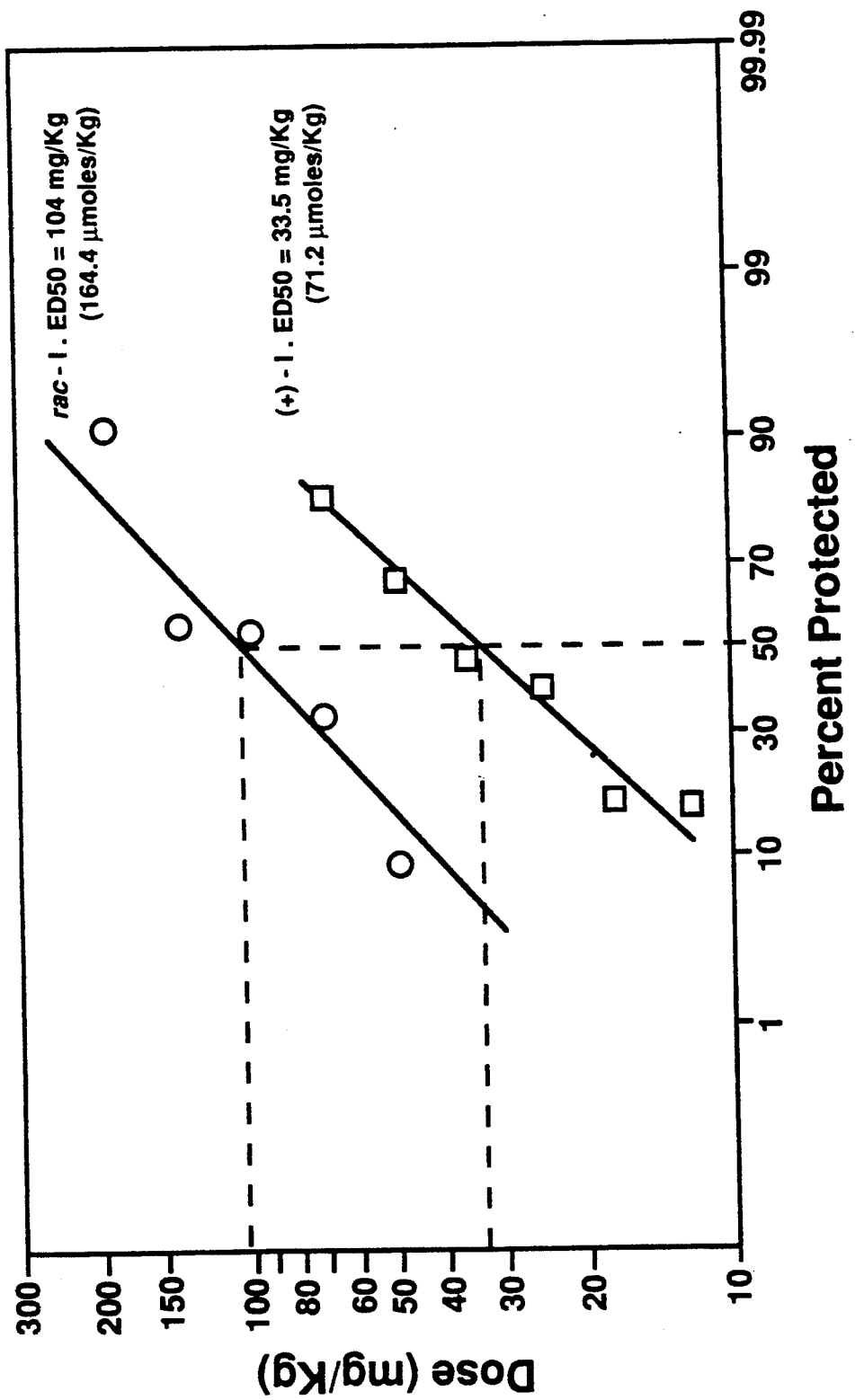
FIG. 12 is the graphical depiction of the antithromboembolic activity of rac-I.2HBr and the (+)IC enantiomer in vivo in mice.

In the mouse antithrombotic model, (+)-I was approximately three times more potent in protecting the mice from thromboembolic death ($ED_{50}$=33.5 mg or 71.2 μmoles/kg compared to the racemic I.2HBr ($ED_{50}$=104 mg or 164.4 μmoles/kg). (FIG. 12)

EFFECT ON CYTOSOLIC IONIZED CALCIUM.

Cytosolic ionized calcium ($Ca^{2+}$)$_i$ plays a key role in stimulus-response coupling in platelets (Rink and Sage, Annu. Rev. Physiol., Vol 52, Pages 431-449, 1990). Agonist binding to platelet receptors is accompanied by a sharp rise in $Ca^{2+}$]$_i$ which originates from one or more dischargeable intracellular stores as well as from the extracellular fluid (Ware, et al., J. Clon. Invest., Vol. 77, Pages 878-886, 1986).

Receptor binding by a number of platelet agonists results in the hydrolysis of phosphatidylinositol 4,5-bisphosphate by phospholipase C to form the second messengers, inositol 1,4,5-trisphosphate (IP3) and diacylglycerol (DG) (Berridege, Biochem. J., Vol. 220, Pages 345-360, 1984). The primary role of IP3 is to release $Ca^{2+}$ from non-mitochondrial stores (Berridge and Irvine, Nature, vol. 312, Pages 315-321, 1984). The mechanism controlling $Ca^{2+}$-influx is more complex and appears to be mediated by at least three pathways (Rink and Sage, Annu. Rev. Physiol., Vol. 52, Pages 431-449, 1990).

The elevated levels of [$Ca^{2+}$]$_i$ initiate a cascade of events which culminate in platelet aggregation (Seiss, Physiol. Rev., Vol. 69, Page 58-178, 1989). Thus, the platelet aggregation-inhibitory activity of I and related compounds is dependent on restraining the rise of cytosolic ionized calcium.

Procedure for Cytosolic Ionized Calcium Determination. The basic procedure of Yamaguchi, et al. (Thromb. Res., Vol. 44, Pages 165-174, 1986) was followed. Blood was collected from six blood donors, aged 24-38 years, who had fasted overnight and affirmed abstinence from alcohol, caffeine and medications of any kind for a period of at least one week prior to donation. Platelet rich plasma (PRP) was obtained by centrifugation (120 g, 15 min) of citrated venous blood (3.8% trisodium citrate, final concentration) and 1.0 M citric acid, 0.009 of the volume of PRP, was added. Platelets were collected (800 g, 15 min), resuspended in and washed (800 g, 15 min) with HEPES-buffered saline (140 mM NaCl, 2.7 mM KCl, 0.1% bovine albumin, 0.5% glucose, 3.8 mM HEPES, pH 7.6) with EGTA (5 mM) and $PGE_1$ (1 μM). The platelet pellet was resuspended in 90 μl of the same buffer and added to 20μl of 3 mg/ml aequorin solution in a 1.5 ml Eppendorf centrifuge tube. Six 1 μl aliquots of DMSO were added at 90 second intervals with brief, gentle mixing on a Vortex mixer and the platelet suspension was incubated 2 minutes after the last addition. One ml of HEPES-buffered saline was added, gently mixed, and again incubated for 2 minutes. The platelets were pelleted (1000 g, 30 sec), resuspended in HEPES-buffered saline to which was added either 1 mM Mg $Cl_2$, (calcium-free buffer) or 1 mM Mg $Cl_2$ and 1 mM Ca $Cl_2$ (calcium buffer), depending on the experiment. The platelet count was adjusted to $3-4\times10^5$ platelets/μl.

The Platelet Ionized Calcium Aggregometer (Chrono-Log Corp., Ltd., Havertown, Pa.) was used to obtain simultaneous aggregation and luminescence data under the following experimental conditions: (1) platelet suspension, 1 ml, was equilibrated at 37° C. with stirring at 1100 rpm; (2) 100 μl (1.2 μg) of fibrinogen was added; (3) the vehicle (95% ethanol) or the test compound in vehicle was added; (4) when needed, 10 μl of the desired concentration of EGTA was added 30 seconds prior to addition of the agonist; then (5) the agonist (Collagen, 5 μg or 20 μg) was added and the time noted. At one minute after addition of the agonist in Channel 1, a platelet sample containing fibrinogen in Channel 2 was lysed with 10 μl of a 1:1 solution of Triton X-100 (final concentration 0.005%) 10 mM $CaCl_2$ (final concentration 0.5 mM). Treated and control fluorescence data were corrected for time dependent decay of fluorescence using data from the untreated lysed controls.

Normally 4 compound-treated samples (at 4 different concentrations) interspersed with 3 control samples were evaluated at 4.5 minute intervals starting 18-23 minutes after the DMSO treatment. The $Ia_{50}$ values were calculated as described earlier. The compound concentrations effecting 50% inhibition ($Ica_{50}$) of collagen-induced cytosolic ionized calcium values was determined by linear regression analysis.

Compounds I-rac, (+)−I,(IC) and (−)−I(IA) were evaluated. The $Ia_{50}$ (collagen-induced aggregation) and $Ica_{50}$ (compound concentration required to inhibit by 50% the collagen-induced rise in cytosolic ionized calcium)values determined with platelet suspensions in HEPES-buffered saline containing 1.0 mM $CaCl_2$ were as follows:

| Compound | Ia$_{50}$($\mu$M) $\pm$ S.E. ADP-Induced (n = 5-6) | Ia$_{50}$($\mu$M) $\pm$ S.E. Collagen-induced (n = 4) | Ica$_{50}$($\mu$M) $\pm$ S.E. Collagen-induced (1mM[Ca$^{2+}$]$_o$) (n = 4) |
|---|---|---|---|
| I rac-I | 44.5 + 12.7 | 20.2 + 3.7 | 21.2 + 5.1 |
| IA (−)-I | 233.4 + 52.1 | 198.8 + 29.4 | 170.8 + 38.4 |
| IB (0)-I | 41.4 + 11.8 | 65.7 + 18.3 | 24.3 + 3.8 |
| IC (+)-I | 15.3 $\pm$ 3.9 | 10.7 $\pm$ 2.7 | 3.6 $\pm$ 1.2 |

[Ca$^{2+}$]$_o$ indicates an external medium. i.e., calcium was added to the medium.

As can be seen from the data, compared to (−)−I, (+)−I was 15 times more potent in inhibiting aggregation in vitro when ADP was the agonist and 18 times more potent with collagen as the agonist. Also, IC is much more potent than racemic I, I-A and IB in inhibiting the rise of cytosolic ionized calcium. (+)−I was also 2 to 3 times more potent than rac-I.

Figure 13:
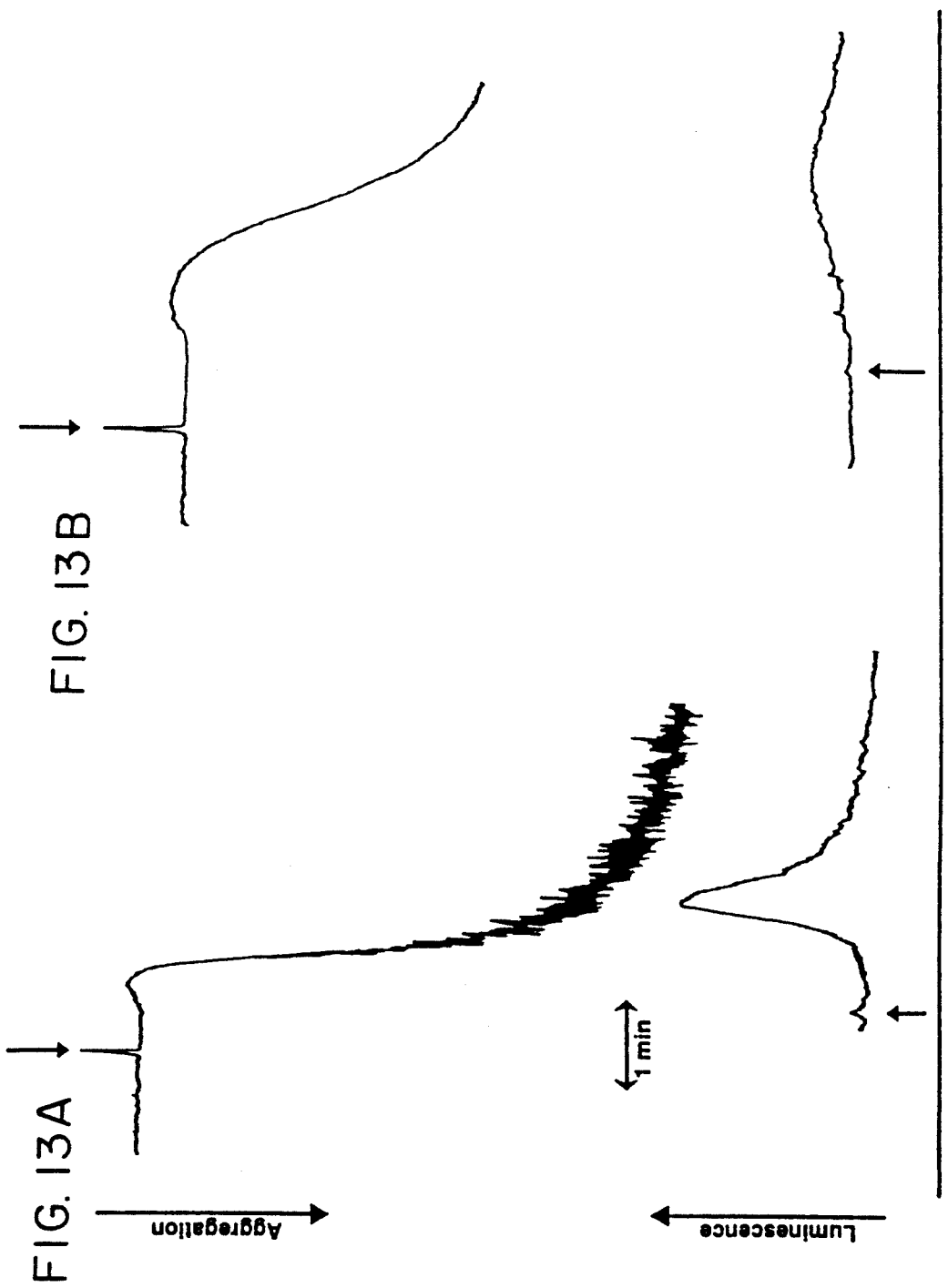
FIG. 13 shows representative tracings of aggregation and aequorin-indicated [Ca²⁺] response by human platelets suspended in HEPES-buffered saline containing 1.0 mM Ca²⁺. Collagen (5.0 μg) was added at the time indicated by the arrows. The platelet suspension (1.0 ml) was pre-incubated for 1.0 min. with 1.0 μl of (A) 95% ethanol or (B) 36 μM Compound I in 95% ethanol. Luminescence was recorded at a gain of 0.2.
Figure 14:
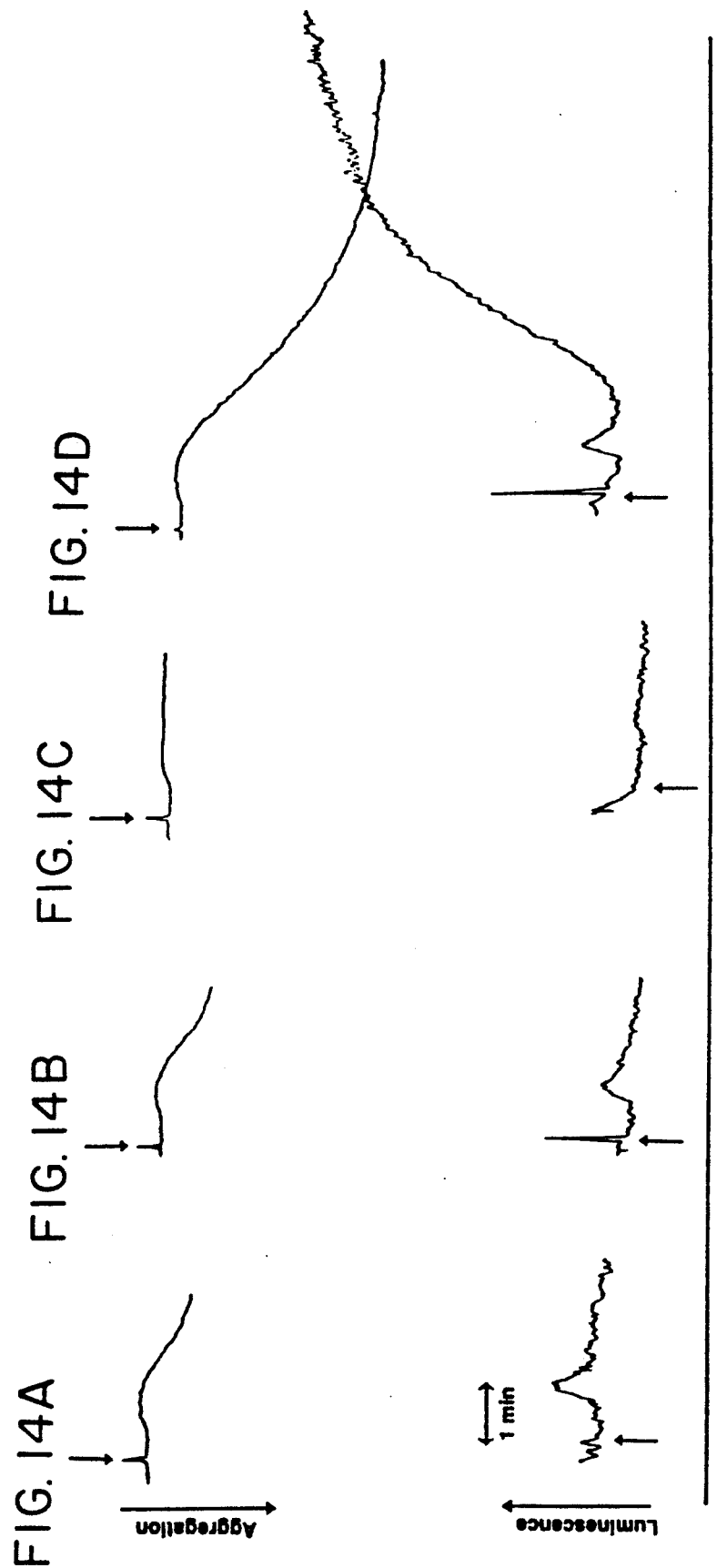
FIG. 14 depicts aggregation and [Ca²⁺]ᵢ mobilization in the presence of (A) 1.0 mM EGTA, (B) 2.0 mM EGTA, (C) 2.0 mM EGTA added 30 seconds after pre-incubation of the platelet preparation with 9.3 μM Compound I, (D) 0.1 mM EGTA. Collagen (20 μg) was added at times indicated by the arrows. Luminescence was recorded at a gain of 0.5.

Since these experiments were carried out in Ca$^{2+}$-containing media, the influence of the present compounds could be due to their action on the intracellular discharge of sequestered calcium (by organelles such as the dense tubular system), and/or on transmembrane flux (FIG. 11). FIG. 13 depicts representative tracings of aggregation and aequorin-indicated [Ca$^{2+}$] response by human platelets suspended in HEPES-buffered saline containing 1.0 mM Ca$^{2+}$. Collagen (5.0 $\mu$g) was added at the time indicated by the arrows. The platelet suspension (1.0 ml) was pre-incubated for 1.0 min. with 1.0 $\mu$l of (A) 95% ethanol or (B) 36 $\mu$M Compound I in 95% ethanol Luminescence was recorded at a gain of 0.2. FIG. 14 depicts the aggregation and [Ca$^{2+}$] mobilization in the presence of (A) 1.0 mM EGTA, (B) 2.0 mM EGTA, (C) 2.0 mM EGTA added 30 seconds after pre-incubation of the platelet preparation with 9.3 $\mu$M Compound I, (D) 0.1 mM EGTA. Collagen (20 $\mu$g) was added at time indicated by the arrows. Luminescence was recorded at a gain of 0.5.

Figure 15:
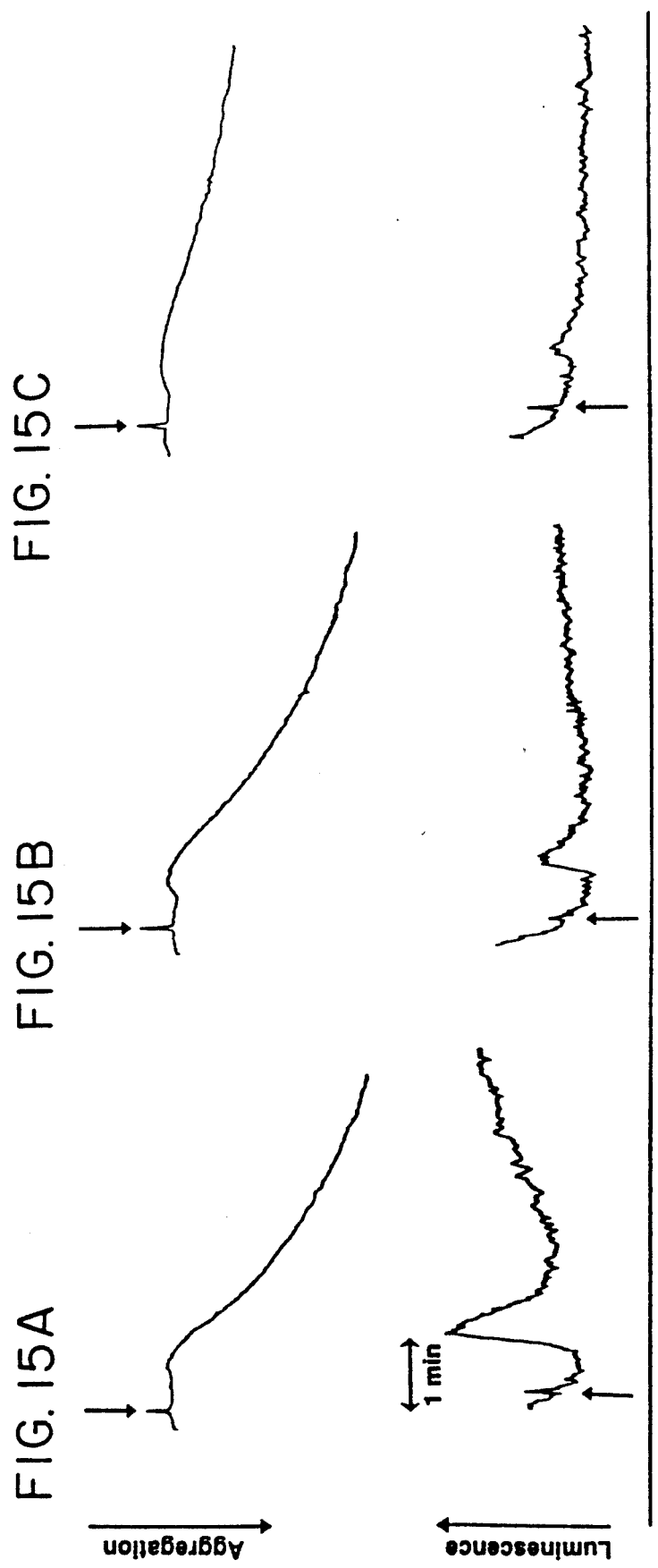
FIG. 15 shows representative tracings of aggregation and [Ca²⁺] mobilization in the presence of 0.1 mM EGTA. The platelet suspension (1.0 ml) was pre-incubated with 1.0 μl of (A) 95% ethanol, (B) a solution of Compound I (14.59 μM) in 95% ethanol, or (C) a solution of Compound I (23.87 μM) in 95% ethanol. Collagen (20 μg) was added at time indicated by the arrows. (Luminescence was recorded at a gain of 0.5).

Collagen-stimulation of platelets suspended in media containing 1.0 mM of Ca$^{2+}$ (FIG. 13) or 1.0 mM (FIG. 14A) or 2.0 mM (FIG. 14B) EGTA (a calcium chelator) gave some cytosolic ionized calcium peak (aequorin-indicated luminescence). Contrarily, two phases of Ca$^{2+}$ mobilization were observed when aequorin-loaded human platelets suspended in a medium containing 0.1 mM EGTA were stimulated with collagen (FIG. 14, designation D). The first corresponded to platelet shape change and the second peak to aggregation. FIG. 15 shows representative tracings of aggregation and [Ca$^{2+}$]$_i$ mobilization in the presence of 0.1 mM EGTA. The platelet suspension (1.0 ml) was pre-incubated with 1.0 $\mu$l of (A) 95% ethanol, (B) a solution of Compound I (14.59 $\mu$M) in 95% ethanol, or (C) a solution of Compound I (23.87 $\mu$M) in 95% ethanol. Collagen (20 $\mu$g) was added at time indicated by the arrows. Luminescence was again recorded at a gain of 0.5. As the data in FIG. 15 indicates, Compound I inhibited both the platelet shape change peak and the aggregation peak. It is suggested that inhibition of the mobilization of intraplatelet calcium stores as well as blocking of transmembrane Ca-flux appears to be responsible for the platelet aggregation-inhibitory activity. Accordingly, the stereo-selective inhibitory properties of the compounds of the present invention appear to be mediated through the inhibition of [Ca$^{2+}$].

The compounds described herein, and more particularly, the (+) enantiomer of Compound I, has been demonstrated to 15 times more potent than its (−)-antipode and two to three times more potent than the racemic mixture of Compound I. The structure and foregoing data concerning the present compounds also indicate that lower dosages can be employed to achieve satisfactory activity thus lowering the toxicity of the present compounds as compared to those compounds currently in use.

The present new compounds which contain basic nitrogen atoms can form salts with acids. All such acid salts are contemplated by the invention but especially preferred are salts with pharmaceutically acceptable acids, such as hydrohalic, especially hydrobromic and hydrochloric, sulfuric, nitric, toluenesulfonic, acetic, propionic, tartaric, malic and similar such acids well known in this art.

The compounds of the present invention can be employed to inhibit blood platelet aggregation in a blood supply, i.e., for instance, stored blood, by adding a blood platelet aggregation inhibiting amount of the present compounds. Additionally, the present compounds are employable for inhibiting blood platelet aggregation in animals in need thereof, including humans.

The compounds of the present invention can be formulated with suitable pharmaceutically acceptable carriers into unit dosage form and can be administered orally, parenterally or rectally. The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 5 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such a peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene, glycol, and liquid polyethylene glycol and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions ar prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 250 to about 750 mg being preferred. Expressed in proportions, the active compound is generally present in from about 10 to about 750 mg/ml of carrier. In the case of compositions containing supplementary active ingredients, the dosages are determined by reference to the usual dose and manner of administration of the said ingredients.

The following examples further illustrate the present invention. Inasmuch as these examples are provided solely for illustrative purposes the invention should not be limited thereto.

EXAMPLE 1

$\alpha,\alpha'$-Bis[3-(N-benzyl-N-methylcarbamoyl)piperidino]p-xylene (13c)

A. N-benzyl-N-methylnicotinamide (11c). Thionyl chloride (35.7 g, 0.3 mol) was added dropwise to a cold stirred mixture of 36.9 g (0.3 mol) nicotinic acid, 48.5 ml (0.6 mol) of pyridine and 15 mL toluene. After the reaction mixture was gradually heated to, and maintained at 90° C. for 1 h, 36.4 g (0.3 mol) of N-benzylmethylamine in 50 mL toluene was dispensed gradully into the reaction mixture from a dropping funnel. An additional 80 mL of pyridine was added to trap the liberated acid. The stirred mixture was maintained at 60° C. for 3 h and at 90° C. for 1 h, after which the toluene layer containing the product was separated and washed with 4×250 mL of 1N HCl. The pH of the combined aequeous acidic solution was adjusted to 9.0 with 29% aq. $Na_2CO_3$, and the amide was extracted with 4×250 ml of toluene. The extract was dried ($MgSO_4$), filtered and concentrated. The residue was distilled under high vacuum ($bp_{0.050}$ 152°–153° C.) to yield 48.0 g of the amide 11c as a yellowish oil.

B. $\alpha,\alpha'$-Bis[3-(N-benzyl-N-methylcarbamoyl)-pyridinium]-p-xylene dibromide (12c). To a stirred solution of 26.6 g of N-benzyl-N-methyl-nicotinamide (1c, 0.1176 mol) in 350 mL absolute ethanol was added 15.0 g (0.0568 mol) of $\alpha,\alpha'$-dibromo-p-xylene in 200 mL of hot acetone from a hot water-jacketed dropping funnel. After refluxing for 9 h, the solid reaction product was recrystallized from absolute ethanol to give 29.3 g of 12c.

C. $\alpha,\alpha'$-Bis[3-(N-benzyl-N-methylcarbamoyl)-piperidino]-p-xvlene dihydrobromide (13c). Catalytic reduction (0.5 g $PtO_2$) of 12.5 g (0.0174 mol) of 12c in 100 mL ethanol/150 mL water (60 psi, ambient temp.)

followed by recrystallization of the product from absolute ethanol afforded 4.1 g 3c. $^1$H NMR (CDCl$_3$) δ 1.70 (bs, 8H, —CH$_2$—), 2.00–2.95 (m, 8H, —CH$_2$—N—CH$_2$—), 2.90 (S, 6H, —NCH$_3$), 3.50 (S, 4H, N—CH$_2$C$_6$H$_4$), 4.57 (bs, 4H, N—CH$_2$C$_6$H$_5$), 7.30, 7.27 (Two S, 14H, Ar-H).

D. Resolution of the Product of IC. The product of Example Ic was dissolved in 10% ethanol in 0.025 M phosphate buffer (pH 7.0) containing 0.025 M tetrabutylammonium (TBA)-HSO$_4$. The various enantiomers were separated by HPLC on a chiral-AGP ($α_1$-acid glycoprotein) (5 μm) analytical column (100×4.0 mm). The mobile phase was 10% ethanol in 0.025 M phosphate buffer (pH 7.0) containing 0.025 M tetrabutyl-ammonium (TBA) hydrogen sulfate. The flow rate was 0.9 ml/min.

Three stereoisomers were isolated, identified as A, B and C. When the circular dichroic spectra were taken, a negative CD cotton effect was observed for compound 13c-A, a positive CD cotton effect was observed for compound 13c-C, and no CD cotton effect was observed for compound 13c-B.

EXAMPLE 2

α,α′-Bis[3-(N,N-diethylaminomethyl)-piperidino]-p-xylene tetrahydrochloride (4)

A solution of α,α′-bis[3-N,N-diethylcarbamoyl)piperdino]-p-xylene dihydrobromide(I) (8.2 g) in water was adjusted to pH 9.0 with aq. 29% Na$_2$CO$_3$, and extracted with ether. Ether was removed by evaporation and the residue was recrystallized from ethyl acetate to yield 4.0 g of I free base, mp 122.5°–126° C.

To a solution of LiAlH$_4$ (12.24 g) in anhyd. THF (270 mL) I free base (34.5 g) in anhyd. THF (400 mL) was added dropwise while stirring, and the reaction mixture was refluxed at 66.5° C. for 19 h under N$_2$. After cooling to room temp., 97 mL of 20% NaOH was added while stirring and maintaining the reaction mixture at 24°–29° C. After vigorous stirring for an additional 20 min the semisolid was filtered off and discarded, and the filtrate was extracted with 3×100 mL of THF. The combined extract was dried (anhyd. Na$_2$SO$_4$), filtered and evaporated, and the resulting oil was subjected to fractional vacuum distillation. Free base 4 (20.7 g) was collected at bp$_{0.07}$ 213°–216° C. $^1$H NMR (CDCl$_3$) 0.97 (t, J=7Hz, 12H, CH$_3$), 1.67 (m, 8H, NCH$_2$), 2.44 (q, J=7Hz, NCH$_2$CH$_3$), 3.46 (d, J=3Hz, 4H, NCH$_2$C$_6$H$_4$), 7.27 (s,4H, C$_6$H$_4$).

A solution of free base 4 (20.0 g) in 500 mL anhyd. ether was acidified to pH 5.0 with a saturated solution of dry HCl gas in diethyl ether at 0° C. and the precipitate was recrystallized from a mixture of ethanol:ethyl acetate (2:3) to yield 10 g of 4.

The above-identified compound is resolved and the various enantiomers are separated in accordance with the procedure described in Example 1 and/or on pages 19–26 of the present specification.

EXAMPLE 3

α,α′-Bis[3-(N-benzylcarbamoyl)piperidino]p-xylene dihydrobromide (5)

The above compound was prepared in accordance with the procedure described in Example 1, except N-benzylamine is used instead of N-benzylmethylamine.

The above-identified compound is resolved and the various stereoisomers are separated in accordance with the procedure described in Example 1 or on pages 19–26 of the present application.

EXAMPLE 4

α,α′-Bis[3-(N-benzyl-N-ethylcarbamoyl)piperidino]-p-xylene dihydrobromide (6)

The above-identified compound was prepared in accordance with the procedure described in Example 1, except N-benzylethylamine is used instead of N-benzylamine. In addition, the hydrogenation step as described in Example 1c was carred at 50° C.

The above-identified compound is resolved and the various stereoisomers are separated in accordance with the procedure described in Example 1 or on pages 19–26 of the instant specification.

EXAMPLE 5

α,α′-Bis[3-(N-benzyl-N-propyl carbamoyl)piperidino]p-xylene dihydrobromide (7)

The above-identified compound was prepared in accordance with the procedure described in Example 1 except N-benzylpropylamine was used instead of N-benzylamine (see Example 1a). In addition, the hydrogenation was carried out in accordance with the procedure described in Example 1c, except it was carried out at 50° C.

The above-identified compound is resolved and the various stereoisomers are separated in accordance with the procedure described in Example 1 or on pages 19–26 of the instant specification.

EXAMPLE 6

α,α′-Bis[3-(N,N-dibenzylcarbamoyl)piperidino] p-xYlene dihydrobromide (8)

The above-identified compound was prepared in accordance with the procedure described in Example 1, except N,N-dibenzylamine was used in place of N-benzylmethylamine (see Example 1a). Further, the hydrogenation was carried out in accordance with the procedure described in Example 1c, except it was carried out at 50° C.

The above-identified compound is resolved and the stereoisomers are separated in accordance with the procedure described in Example 1 or on pages 19–26 of the instant specification.

EXAMPLE 7

α,α′-Bis[3-(N-methyle-N-butyl carbamoyl)piperidino] p-xylene dihydrobromide (9)

The above-identified compound was prepared in accordance with the procedure described in Example 1, except that N-methylbutylamine was used in place of N-benzylmethylamine (See Example 1c).

The above-identified compound is resolved and the stereoisomers are separated in accordance with the procedure in Example 1 or on pages 19–26 of the instant specification.

EXAMPLE 8

α,α′-Bis[3-(piperidino carbonyl)piperidino] p-xylene dihydrobromide (10)

The above-identified compound was prepared in accordance with the procedure in Example 1 except piperidine was used in place of N-benzylmethylamine.

This compound is resolved and separated into its stereoisomers in accordance with the procedure in Example 1 or on pages 19-26 of the instant specification.

Compounds 13(c) and 10 were also tested for their in-vitro platelet aggregation-Inhibitory Activity in accordance with the assay described on pages 25-28 of the instant specification. The results are tabulated below:

| Compound | Ia$_{50}$(μm) ± S.E. ADP-induced | # of individual determinations |
|---|---|---|
| 13c-A(−) | 57.37 ± 6.01 | 5 |
| 13c-B(0) | 46.93 ± 8.37 | 5 |
| 13c-C(+) | 9.55 ± 1.47 | 5 |
| 13c rac* | 27.31 ± 3.23 | 7 |
| 10 rac* | 28.85 ± 8.96 | 5 |

*rac = racemic mixture

Figure 16:
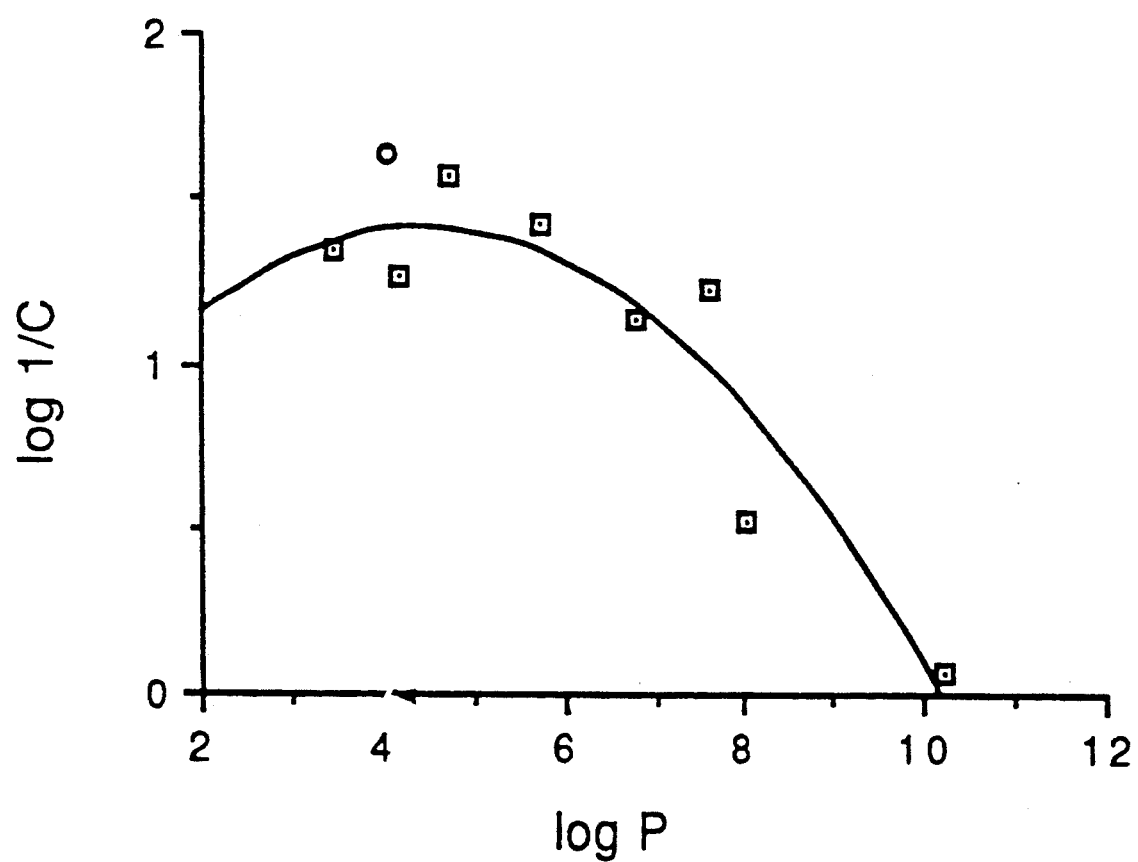
FIG. 16 illustrates the graphical relationship between platelet aggregation-inhibitory activity (log I/C) and hydrophobicity (log P) of carbamoylpiperidines.

FIG. 16 depicts the relationship between activity (log 1/C) and hydrophobicity (log P) of racemic compounds of Examples 1-8 and I, wherein $C = IC_{50} \times 10^{-3}$; $IC_{50}$ is the compound concentration which inhibits ADP-induced aggregation by 50%, and P is octanol/water partition coefficient. This plot showed that the parabolic relationship is statistically significant (equation 1).

$$\log(1/C) = 0.387 (\log P) - 0.043(\log P)^2 + 0.545 \quad (1)$$
$$n = 8; \ r = 0.93; \ s = 0.22; \ F_{\alpha = 0.01} = 16.7$$

Thus, the single parameter log P accounts for about 87% ($r^2$ 0.87) of the variance of the activities of these derivatives. The data also suggest that hydrophobicity associated with the 3-substituent plays a significant role in influencing the platelet aggregation-inhibitory activity.

From equation 1, the optimum log P value is 4.5. With this parabolic relationship as a model, the derivative 9 was designed (log P, 4.5) with a predicted log 1/C value of 1.6 ($IC_{50}$, 25 M). When this compound was synthesized and evaluated, the observed log 1/C value was 1.7 ($IC_{50}$, 22.1 ± 5.5 μM).

The log P values along with the $IC_{50}$ values of all the test compounds are given in the following Table.

| Platelet Aggregation-Inhibitory Activities and Partition Coefficients of Carbamoylpiperdines | | | | |
|---|---|---|---|---|
| compd (racemic) | LogP[a] | IC$_{50}$(μM ± S.E.)[b] | Log1/C[c] | n |
| 1 | 3.478 | 44.5 ± 12.7 | 1.352 | 6 |
| 5 | 4.176 | 53.6 ± 5.3 | 1.271 | 6 |
| 13c | 4.718 | 27.3 ± 3.2 | 1.564 | 7 |
| 6 | 5.756 | 37.7 ± 4.6 | 1.424 | 7 |
| 7 | 6.794 | 72.9 ± 20.8 | 1.138 | 5 |
| 8 | 8.034 | 302.6 ± 60.8 | 0.519 | 5 |
| 5[d] | 7.630 | 58.7 | 1.231 | — |
| 6[e] | 10.202 | 862.2 | 0.064 | — |
| 4 | 4.80 | 156.0 ± 459.9 | −0.195 | 4 |
| 9 | 4.516 | 22.1 ± 5.5 | 1.656 | 6 |

[a]Octanol/water partition coefficients using PROLOG version 4.1e, CompuDrug Inc.
[b]Compound concentration which inhibits ADP-induced platelet aggregation by 50%.
[c]C = IC$_{50}$ × $10^{-3}$. [d]α,α'-bis[3-(N,N-dibutylcarbamoyl)-piperidino]p-xylene dihydrobromide.
[d]α,α'-bis[3-(N,N-dibutylcarbamoyl)piperidino]p-xylene dihydrobromide.
[e]α,α'bis[3-(N-decylcarbamoyl)piperidino]-p-xylene dihydrobromide.
n = Number of individuals determinations.

Thus, as showed hereinabove, the value of logP can vary from between 2.00 and 11.00. However, it is preferred that logP varies from about 3.0 to about 5.0 and more preferred if it varies from about 3.5 to about 5.0. The most preferred value is approximately 4.5.

The foregoing description of the invention has been presented for purposes of illustration and description and is not intended to be exhaustive or to limit the invention to the precise form disclosed. Other variations are possible in light of the teachings presented herein.

The embodiments of this invention in which an exclusive property or privilege is claimed are defined as follows:

We claim:

1. Substantially pure stereoisomers of a compound of the formula:

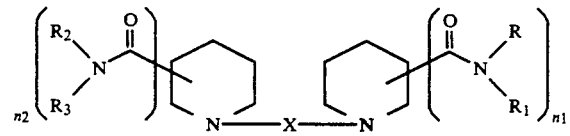

wherein $n_1$ and $n_2$ are the same or different and are 1 or 2; X is alkyl ($C_1$-$C_{10}$), aryl ($C_6$-$C_{10}$) or aralkyl ($C_7$-$C_{12}$); and wherein R, $R_1$, $R_2$ and $R_3$ are the same or different and are chosen from H, alkyl ($C_1$-$C_{10}$), aryl ($C_6$-$C_{10}$), aralkyl ($C_7$-$C_{12}$), or a heterocyclic group, or R and $R_1$ taken together with the nitrogen atom to which they are attached form a 5- or 6-membered heterocyclic ring or $R_2$ and $R_3$ taken together with the nitrogen atom to which they are attached form a 5- or 6-membered heterocyclic ring or addition salts thereof with pharmaceutically acceptable acids.

2. The compound according to claim 1 which exhibits, in the light absorbing region, a (+) cotton effect in circular dichroic spectra.

3. The compound according to claim 1 which exhibits, in a light absorbing region, a (−) cotton effect in circular dichroic spectra.

4. The compound according to claim 1 in its S,S configuration.

5. The compound according to claim 1 in its R,R configuration.

6. The compound according to any one of claims 1-5 wherein R, $R_1$, $R_2$ and $R_3$ are the same or different and are chosen from alkyl ($C_1$-$C_5$) or aralkyl.

7. The compound according to any one of claims 1-5 wherein X is aralkyl ($C_7$-$C_{12}$).

8. The compound according to any one of claims 1-5 wherein R=$R_2$ and $R_1$=$R_3$.

9. The compound according to any one of claims 1-5 wherein R, $R_1$, $R_2$ and $R_3$ are the same or are different and are chosen from methyl, ethyl, propyl, butyl or benzyl.

10. The compound according to any one of claims 1-5 wherein R, $R_1$, $R_2$ and $R_3$ are all ethyl or R and $R_2$ are benzyl and $R_1$ and $R_3$ are methyl.

11. The compound according to any one of claims 1-5 wherein X is

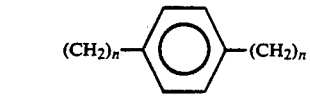

wherein each n is 1, 2, 3, 4, or 5.

12. The compound according to claim 11 wherein each n is equal to 1.

13. The compound according to claim 1 wherein $n = n_2 = 2$.

14. A substantially pure stereoisomer of a compound of the formula:

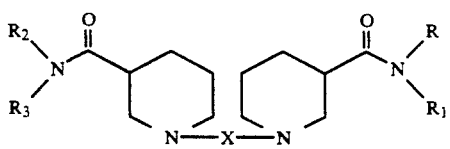

wherein X is alkyl ($C_1$-$C_{10}$), aryl ($C_6$-$C_{10}$) or aralkyl ($C_7$-$C_{12}$); and, wherein R, $R_1$, $R_2$ and $R_3$ are the same or different and are chosen from H, alkyl ($C_1$-$C_{10}$), aryl ($C_6$-$C_{10}$), aralkyl ($C_7$-$C_{12}$), or a heterocyclic group, or R and $R_1$ taken together with the nitrogen atom to which they are attached or $R_2$ and $R_3$ taken together with the nitrogen atom to which they are attached form a heterocyclic ring or addition salts thereof pharmaceutically acceptable acids.

15. The compound according to claim 14 which exhibits, in the light absorbing region, a (+) cotton effect in circular dichroic spectra.

16. The compound according to claim 14 which exhibits, in a light absorbing region, a (−) cotton effect in circular dichroic spectra.

17. The compound according to claim 14 in its S,S configuration.

18. The compound according to claim 14 in its R,R configuration.

19. The compound according to any one of claims 14–18 wherein R, $R_1$, $R_2$ and $R_3$ are the same or different and are chosen from alkyl ($C_1$-$C_5$) or aralkyl.

20. The compound according to any one of claims 14–18 wherein X is aralkyl ($C_7$-$C_{12}$).

21. The compound according to any one of claims 14–18 wherein R, $R_1$, $R_2$ and $R_3$ are the same or different and are chosen from methyl, ethyl, propyl, butyl or benzyl.

22. The compound according to any one of claims 14–18 wherein R, $R_1$, $R_2$ and $R_3$ are all ethyl or R and $R_2$ are benzyl and $R_1$ and $R_3$ are methyl.

23. The compound according to any one of claims 14–18 wherein X is

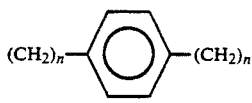

wherein each n is 1, 2, or 3.

24. The compound according to claim 23 wherein each n is equal to 1 or 2.

25. The compound according to any one of claims 14–18 wherein R=$R_2$ and $R_1$=$R_3$.

26. A substantially pure stereoisomer of a compound of the formula:

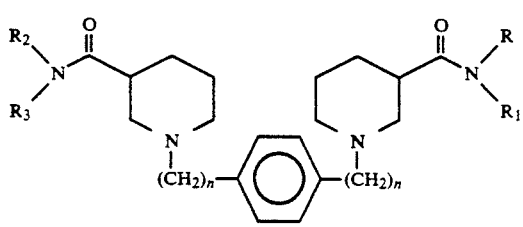

wherein each n=1–5, and R, $R_1$, $R_2$ and $R_3$ are the same or different and are chosen from H, alkyl ($C_1$-$C_{10}$), aryl ($C_6$-$C_{10}$), aralkyl ($C_7$-$C_{12}$) or a heterocyclic group, or R and $R_1$ taken together with the nitrogen atom to which they are attached form a 5- or 6-membered heterocyclic ring or $R_2$ and $R_3$ taken together with the nitrogen atom to which they are attached form a 5- or 6-membered heterocyclic ring or addition salts thereof with pharmaceutically acceptable acids.

27. The compound according to claim 26 which exhibits, in the light absorbing region, a (+) cotton effect in circular dichroic spectra.

28. The compound according to claim 26 which exhibits, in a light absorbing region, a (−) cotton effect in circular dichroic spectra.

29. The compound according to claim 26 in its S,S configuration.

30. The compound according to claim 26 in its R,R configuration.

31. The compound according to any one of claims 26–30 wherein R, $R_1$, $R_2$ and $R_3$ are the same or different and are chosen from alkyl ($C_1$-$C_5$) or aralkyl.

32. The compound according to any one of claims 26–30 wherein R, $R_1$, $R_2$ and $R_3$ are different or are the same and are chosen from methyl, ethyl, propyl, butyl or benzyl.

33. The compound according to any one of claims 26–30 wherein R, $R_1$, $R_2$ and $R_3$ are all ethyl or R and $R_2$ are benzyl and $R_1$ and $R_3$ are methyl.

34. The compound according to claim 26 wherein each n is equal to 1–4.

35. The compound according to any one of claims 6–30 wherein R=$R_2$ and $R_1$=$R_3$.

36. A substantially pure stereoisomer of a compound of the formula:

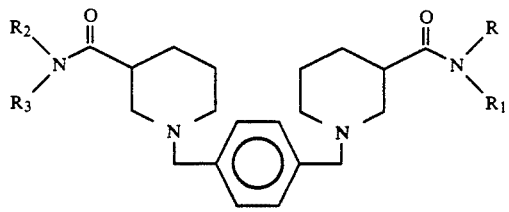

wherein R, $R_1$, $R_2$ and $R_3$ are the same or different and are chosen from H, alkyl ($C_1$-$C_{10}$), aryl ($C_6$-$C_{10}$), aralkyl ($C_7$-$C_{12}$) or a heterocyclic group, or R and $R_1$ taken together with the nitrogen atom to which they are attached form a 5- or 6-membered heterocyclic ring or $R_2$ and $R_3$ taken together with the nitrogen atom to which they are attached form a 5- or 6-membered heterocyclic ring or addition salts thereof with pharmaceutically acceptable acids.

37. The compound according to claim 36 which exhibits, in the light absorbing region, a (+) cotton effect in circular dichroic spectra.

38. The compound according to claim 36 which exhibits, in a light absorbing region, a (−) cotton effect in circular dichroic spectra.

39. The compound according to claim 36 in its S,S configuration.

40. The compound according to claim 36 in its R,R configuration.

41. The compound according to any one of claims 36–40 wherein R, $R_1$, $R_2$ and $R_3$ are the same or different and are chosen from alkyl ($C_1$-$C_5$) or aralkyl.

42. The compound according to any one of claims 36-40 wherein R, $R_1$, $R_2$ and $R_3$ are the same or are different and are chosen from methyl, ethyl, propyl, butyl or benzyl.

43. The compound according to any one of claims 36-40 wherein R, $R_1$, $R_2$ and $R_3$ are all ethyl.

44. The compound according to any one of claims 36-40 wherein $R=R_2$ and $R_1=R_3$:

45. A substantially pure stereoisomer of the compound $\alpha,\alpha'$-Bis[3-(N,N-diethylcarbamoyl)piperidino]-p-xylene, $\alpha,\alpha'$-Bis[3-(N-benzyl-N-methyl-carbamoyl)-piperidino] xylene, $\alpha,\alpha'$-Bis[3-N-methyl, N-butylcarbamoyl)piperidino] p-xylene-or $\alpha,\alpha'$-Bis[3-piperidino carbonyl)piperidino]p-xylene or addition salts thereof with pharmaceutically acceptable acids.

46. The compound of claim 45 which exhibits, in the light absorbing region, a (+) cotton effect in circular dichroic spectra.

47. The compound of claim 45 which exhibits, in the light absorbing region, a (−) cotton effect in circular dichroic spectra.

48. The compound according claims 45 in its S,S configuration.

49. The compound according to claim 45 in its R,R configuration.

50. A substantially pure stereoisomer of the compound $\alpha,\alpha'$-Bis[3-N,N-(diethylcarbamoyl)piperidino]-p-xylene dihydrobromide, $\alpha,\alpha'$-Bis[3-(N-benzyl-N-methylcarbamoyl)piperidino] p-xylene dihydrobromide, $\alpha,\alpha'$-Bis[3-(N-methyl, N-butyl carbamoyl)-piperidino]p-xylene dihydrobromide or $\alpha,\alpha'$-Bis[3-piperidinocarbonyl)piperidino]p-xylene dihydrobromide.

51. A compound of claim 50 which exhibits, in the light absorbing region, a (+) cotton effect in circular dichroic spectra.

52. A compound of claim 50 which exhibits, in light absorbing region a (−) cotton effect in circular dichroic spectra.

53. The compound according to claim 50 in its S,S configuration.

54. The compound according to claim 50 in its R,R configuration.

55. A substantially pure stereoisomer of a compound of the formula:

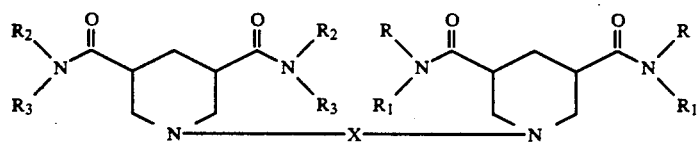

wherein X is alkyl ($C_1-C_{10}$), aryl ($C_6-C_{10}$) or aralkyl ($C_7-C_{12}$); and, wherein each R, $R_1$, $R_2$ and $R_3$ is the same or different and is chosen from H, alkyl ($C_1-C_{10}$), aryl ($C_6-C_{10}$), aralkyl ($C_7-C_{12}$), or a heterocyclic group, or R and $R_1$ taken together with the nitrogen atom to which they are attached form a 5- or 6-membered heterocyclic ring or $R_2$ and $R_3$ taken together with the nitrogen atom to which they are attached form a 5- or 6-membered heterocyclic ring or addition salts pharmaceutically acceptable acids.

56. The compound according to claim 55 which exhibits, in the light absorbing region, a (+) cotton effect in circular dichroic spectra.

57. The compound according to claim 55 which exhibits, in a light absorbing region, a (−) cotton effect in circular dichroic spectra.

58. The compound according to claim 55 in its S,S, S,S configuration.

59. The compound according to claim 55 in its R,R, R,R configuration.

60. The compound according to any one of claims 55-59 wherein $R=R_2$ and $R_1=R_3$.

61. The compound according to any one of claims 55-59 wherein R, $R_1$, $R_2$ and $R_3$ are the same or different and are chosen from alkyl ($C_1-C_5$) or aralkyl.

62. The compound according to any one of claims 55-59 wherein X is aralkyl ($C_7-C_{12}$).

63. The compound according to any one of claims 55-59 wherein R, $R_1$, $R_2$ and $R_3$ are the same or are different and are chosen from methyl, ethyl, propyl, butyl or benzyl.

64. The compound according to any one of claims 55-59 wherein R, $R_1$, $R_2$ and $R_3$ are all ethyl or R and $R_2$ are benzyl and $R_1$ and $R_3$ are methyl.

65. The compound according to any one of claims 55-59 wherein X is

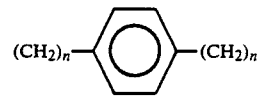

wherein each n is 1, 2, 3, 4 or 5.

66. The compound according to claim 65 wherein each n is equal to 1 or 2.

67. A substantially pure stereoisomer of a compound of the formula:

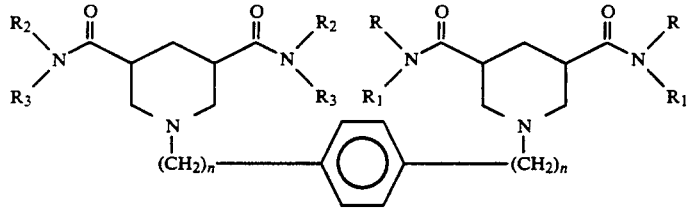

wherein each n=1-4, and each R, $R_1$, $R_2$ and $R_3$ is the same or different and is chosen from alkyl ($C_1-C_{10}$), aryl ($C_6-C_{10}$), aralkyl ($C_7-C_{12}$) or a heterocyclic group, or R and $R_1$ taken together with the nitrogen atom to which they are attached form a 5- or 6-membered heterocyclic ring or $R_2$ and $R_3$ taken together with the nitrogen atom to which they are attached form a 5- or 6- membered heterocyclic ring or addition salts thereof with pharmaceutically acceptable acids.

68. The compound according to claim 67 which exhibits, in the light absorbing region, a (+) cotton effect in circular dichroic spectra.

69. The compound according to claim 67 which exhibits, in a light absorbing region, a (−) cotton effect in circular dichroic spectra.

70. The compound according to Clam 67 in its S,S, S,S configuration.

71. The compound according to claim 67 in its R,R, R,R configuration.

72. The compound according to any one of claims 67-71 wherein R, $R_1$, $R_2$ and $R_3$ are the same or different and are chosen from alkyl ($C_1$-$C_5$) or aralkyl.

73. The compound according to any one of claims 67-71 wherein R=$R_2$ and $R_1$=$R_3$.

74. The compound according to any one of claims 67-71 wherein R, $R_1$, $R_2$ and $R_3$ are the same and are chosen from methyl, ethyl, propyl, butyl or benzyl.

75. The compound according to any one of claims 67-71 wherein R, $R_1$, $R_2$ and $R_3$ are all ethyl or R and $R_2$ are benzyl and R and $R_3$ are methyl.

76. The compound according to claim 67 wherein each n is equal to 1.

77. A method for the inhibition of blood platelet aggregation in a blood supply comprising administering to said blood supply a blood platelet aggregation inhibiting amount of a compound according to any one of claims 1, 14, 26, 36, 37, 46, 51, 55 and 67 or addition salts thereof with pharmaceutically acceptable acids.

78. A method for the inhibition of blood platelet aggregation in an animal in need thereof comprising administering to said animal a blood platelet aggregation inhibiting amount of a compound according to any one of claims 1, 14, 26, 36, 37, 46, 51, 55 and 67 or addition salts thereof with pharmaceutically acceptable acids.

79. A pharmaceutical composition in unit dosage form suitable for administration to an animal in need thereof comprising a pharmaceutically acceptable carrier and a blood platelet aggregation inhibiting amount of a compound according to any one of claims 1, 14, 26, 36, 37, 46, 51, 55 and 67 or addition salts thereof with pharmaceutically acceptable acids.

80. The compound according to any one of claims 1-5 wherein R and $R_1$ taken together with the nitrogen to which they are attached form a piperidino or pyrrolidino ring or $R_2$ and $R_3$ taken together with the nitrogen to which they are attached form a piperidino or pyrrolidino ring.

81. The compound according to any one of claims 14-18 wherein R and $R_1$ taken together with the nitrogen to which they are attached form a piperidino or pyrrolidino ring or $R_2$ and $R_3$ taken together with the nitrogen to which they are attached form a piperidino or pyrrolidino ring.

82. The compound according to any one of claims 26-30 wherein R and $R_1$ taken together with the nitrogen to which they are attached form a piperidino or pyrrolidino ring or $R_2$ and $R_3$ taken together with the nitrogen to which they are attached form a piperidino or pyrrolidino ring.

83. The compound according to any one of claims 36-40 wherein R and R taken together with the nitrogen to which they are attached form a piperidino or pyrrolidino ring or $R_2$ and $R_3$ taken together with the nitrogen to which they are attached form a piperidino or pyrrolidino ring.

84. The compound according to any one of claims 55-59 wherein R and $R_1$ taken together with the nitrogen to which they are attached form a piperidino or pyrrolidino ring or $R_2$ and $R_3$ taken together with the nitrogen to which they are attached form a piperidino or pyrrolidino ring.

* * * * *

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 3, lines 1-2: "TBA $HSO_4$" should read as --TBA·$HSO_4$--

Column 3, line 7: "TBA $HSO_4$" should read as --TBA·$HSO_4$--

Column 3, line 14: "I.2HBr" should read as --I·2HBr--

Column 3, line 17: "I.2HBr" should read as --I·2HBr--

Column 3, line 47: "rac-I.2HBr" should read as --rac-I·2HBr--

Column 3, line 65: "[$Ca^{2+}$]" should read as --[$Ca^{2+}$]$_i$--

Column 4, line 19, Formula (II): "$m_2$" should read as --$n_2$--

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 8, lines 20-30:

"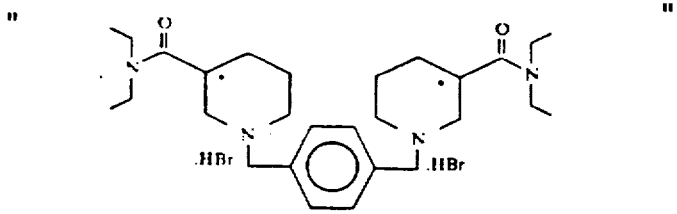"

should read as

--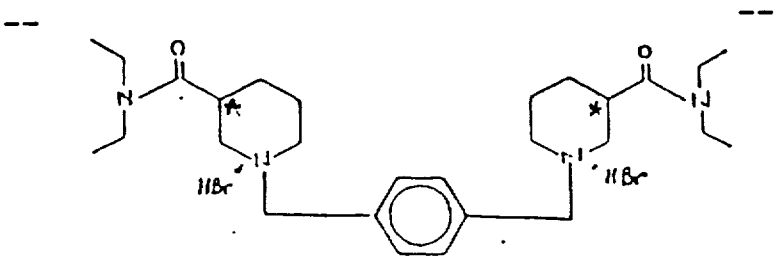--

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 9, lines 31-37:

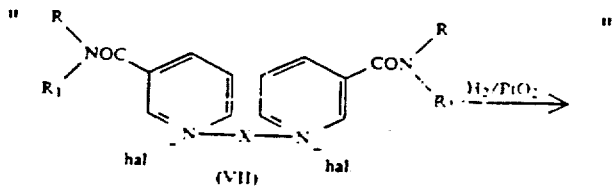

should read as

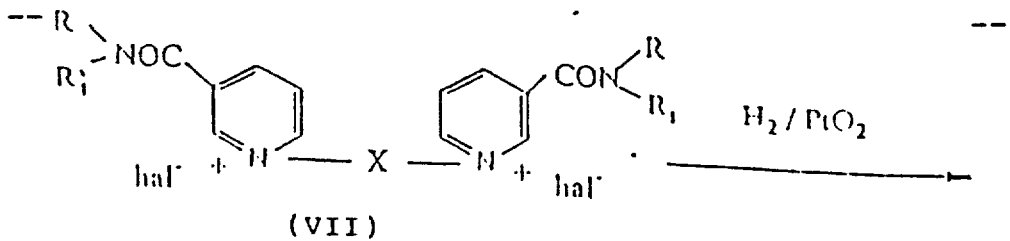

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 10, lines 3-10:

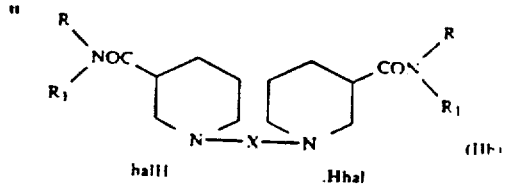

should read as

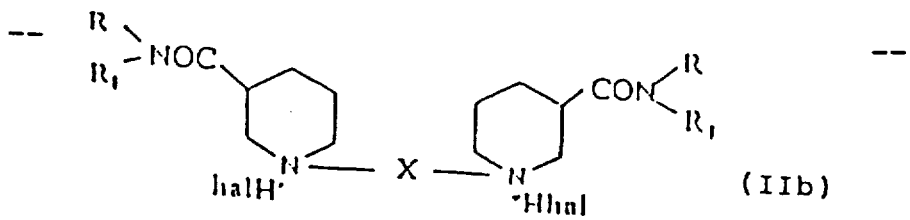

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 10, lines 60-68:

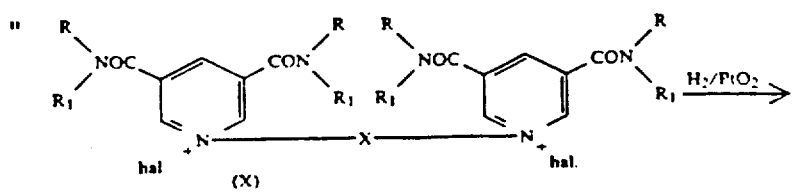

should read as

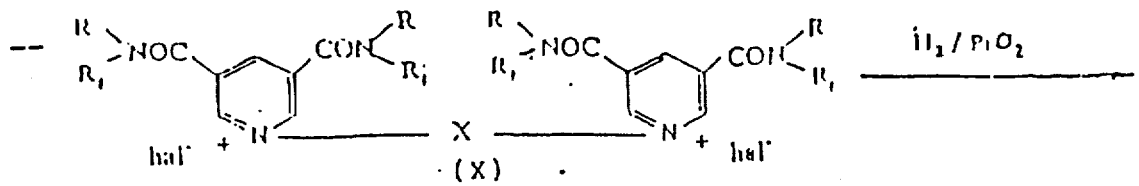

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 11, lines 1-10:

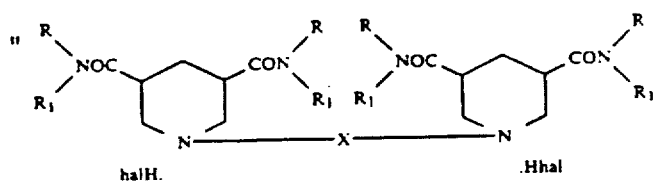

should read as

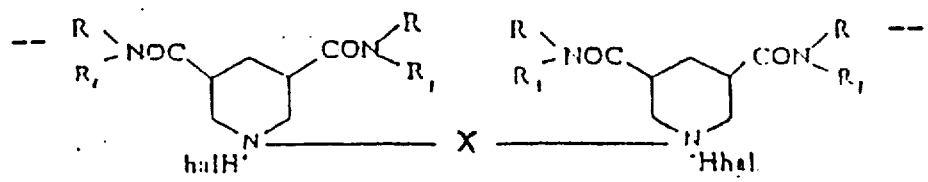

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 12, line 18: after "piperidino" insert --]--

Column 12, line 31: " I.2HBr" should read as --I·2HBr--

Column 13, line 39: "I.2HBr" should read as --I·2HBr--

Column 13, line 42: "I.2HBr" should read as --I·2HBr--

Column 13, line 48: "I.2HBr" should read as --I·2HBr--

Column 14, lines 3-4: "Chira-1AGP" should read as --Chiral-AGP--

Column 14, lines 6-7: "TBA $HSO_4$" should read as --TBA·$HSO_4$--

Column 14, line 33: "I 2HBr" should read as --I·2HBr--

Column 14, line 39: "TBA.$HSO_4$" should read as --TBA·$HSO_4$--

Column 14, line 41: "(I).-2HBr" should read as --(I)·-2HBr--

Column 14, line 43: "I.2HBr" should read as --I·2HBr--

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 14, line 54: "TBA.$HSO_4$" should read as --TBA·$HSO_4$--

Column 15, line 8: "I.D-" should read as --I·D- --

Column 15, line 20: "TBA.$HSO_4$" should read as --TBA·$HSO_4$--

Column 15, line 51: "N" should read as --$N_2$--

Column 17, line 3: "tudied" should read as --studied--

Column 17, line 7: "aqqegometric" should read as --aggegometric--

Column 17, line 37: "I.2HBr" should read as --I·2HBr--

Column 17, line 37: "127" should read as --12.7--

Column 18, line 63: "Rac.I.2HBr" should read as --Rac·I·2HBr--

Column 19, line 40: "I.2HBr" should read as --I·2HBr--

Column 26, line 36: "xYlene" should read as --xylene--

UNITED STATES PATENT AND TRADEMARK OFFICE
CERTIFICATE OF CORRECTION

PATENT NO. : 5,219,867
DATED : June 15, 1993
INVENTOR(S) : Ramachander Gollamudi, et al.

It is certified that error appears in the above-indentified patent and that said Letters Patent is hereby corrected as shown below:

Column 27, line 30: "$(r^2 0.87)$" should read as $--(r^2=0.87)--$

Column 27, line 38: "$IC_{50}$, 25 M" should read as $--IC_{50}$, 25 uM--

Column 28, line 68, Claim 13: "$n=n_2$" should read as $--n_1=n_2--$

Column 30, line 3, Claim 26: "$(C_{7-C12})$" should read as $--(C_7-C_{12})--$

Column 30, line 33, Claim 35: "6-30" should read as --26-30--

Column 31, line 8, Claim 44: ":" should read as --.--

Column 32, lines 3-4, Claim 55: after "salts" insert --thereof with--

UNITED STATES PATENT AND TRADEMARK OFFICE
CERTIFICATE OF CORRECTION

PATENT NO. : 5,219,867

DATED : June 15, 1993

INVENTOR(S) : Ramachanger Gollamudi, et al.

It is certified that error appears in the above-indentified patent and that said Letters Patent is hereby corrected as shown below:

Column 34, line 27, Claim 83: "R and R" should read as --R and $R_1$--.

Signed and Sealed this

Thirtieth Day of August, 1994

Attest:

*Attesting Officer*

BRUCE LEHMAN

*Commissioner of Patents and Trademarks*